(12) United States Patent  (10) Patent No.: US 7,762,445 B2
Heinrich et al.  (45) Date of Patent: Jul. 27, 2010

(54) ELECTROSURGICAL STAPLING APPARATUS

(75) Inventors: Russell Heinrich, Madison, CT (US); Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 12/491,663

(22) Filed: Jun. 25, 2009

(65) Prior Publication Data

US 2009/0261145 A1  Oct. 22, 2009

Related U.S. Application Data

(63) Continuation of application No. 11/707,818, filed on Feb. 16, 2007, now Pat. No. 7,559,453, which is a continuation of application No. 10/513,435, filed as application No. PCT/US03/14520 on May 9, 2003, now Pat. No. 7,207,471, said application No. 12/491,663 is a continuation of application No. 12/363,827, filed on Feb. 2, 2009.

(60) Provisional application No. 60/379,961, filed on May 10, 2002.

(51) Int. Cl.
*A61B 17/10* (2006.01)
(52) U.S. Cl. .................. 227/180.1; 227/19; 227/178.1; 227/175.1; 606/8; 606/144; 606/219
(58) Field of Classification Search ............. 227/175.1, 227/19, 180.1, 178.1; 606/8, 144, 219
See application file for complete search history.

(56) References Cited

U.S. PATENT DOCUMENTS

| 4,485,816 | A | 12/1984 | Krumme |
| 4,550,870 | A | 11/1985 | Krumme et al. |
| 4,672,969 | A | 6/1987 | Dew |
| 5,389,098 | A | 2/1995 | Tsuruta et al. |
| 5,403,312 | A | 4/1995 | Yates et al. |
| 5,529,235 | A | 6/1996 | Boiarski et al. |
| 5,531,744 | A | 7/1996 | Nardella et al. |

(Continued)

FOREIGN PATENT DOCUMENTS

WO  WO 93/08754  5/1993

(Continued)

OTHER PUBLICATIONS

International Search Report for Application PCT/US2003/14520 dated Jun. 10, 2003.

*Primary Examiner*—Brian D Nash

(57) ABSTRACT

An electrosurgical stapling apparatus is provided which uses thermogenic energy as well as surgical fasteners or staples for strengthening tissue, providing hemostasis, tissue joining or welding. The thermogenic energy also strengthens tissue in proximity to a staple line and knife cut line and provides hemostasis along the staple and cut lines formed by the staples and a knife blade during surgical stapling. The use of thermogenic energy provides short-term hemostasis and sealing, and reduces or prevents staple line and cut line bleeding, while the stapling features provide short and long-term tissue strength and hemostasis. The stapling apparatus further substantially reduces or prevents knife cut line bleeding by energizing a knife blade for cauterizing tissue while it is being cut. In one embodiment, energy is applied to the anvil to energize the staples as they make contact with the anvil.

6 Claims, 20 Drawing Sheets

U.S. PATENT DOCUMENTS

| | | |
|---|---|---|
| 5,624,452 A | 4/1997 | Yates |
| 5,658,300 A | 8/1997 | Bito et al. |
| 5,665,085 A | 9/1997 | Nardella |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 6,004,335 A | 12/1999 | Vaitekunas et al. |
| 6,024,741 A | 2/2000 | Williamson, IV et al. |
| 6,030,384 A | 2/2000 | Nezhat |
| 6,162,220 A | 12/2000 | Nezhat |
| 6,488,196 B1 | 12/2002 | Fenton, Jr. |
| 6,602,252 B2 | 8/2003 | Mollenauer |
| 6,626,901 B1 | 9/2003 | Treat et al. |
| 6,905,497 B2 | 6/2005 | Truckai et al. |
| 6,978,921 B2 | 12/2005 | Shelton et al. |
| 6,986,451 B1 | 1/2006 | Mastri et al. |
| 7,011,657 B2 | 3/2006 | Truckai et al. |
| 7,032,799 B2 | 4/2006 | Viola et al. |
| 2002/0190093 A1 | 12/2002 | Fenton, Jr. |
| 2004/0073256 A1 | 4/2004 | Marchitto et al. |
| 2005/0159778 A1 | 7/2005 | Heinrich et al. |

FOREIGN PATENT DOCUMENTS

| | | |
|---|---|---|
| WO | WO 03/094745 | 11/2003 |

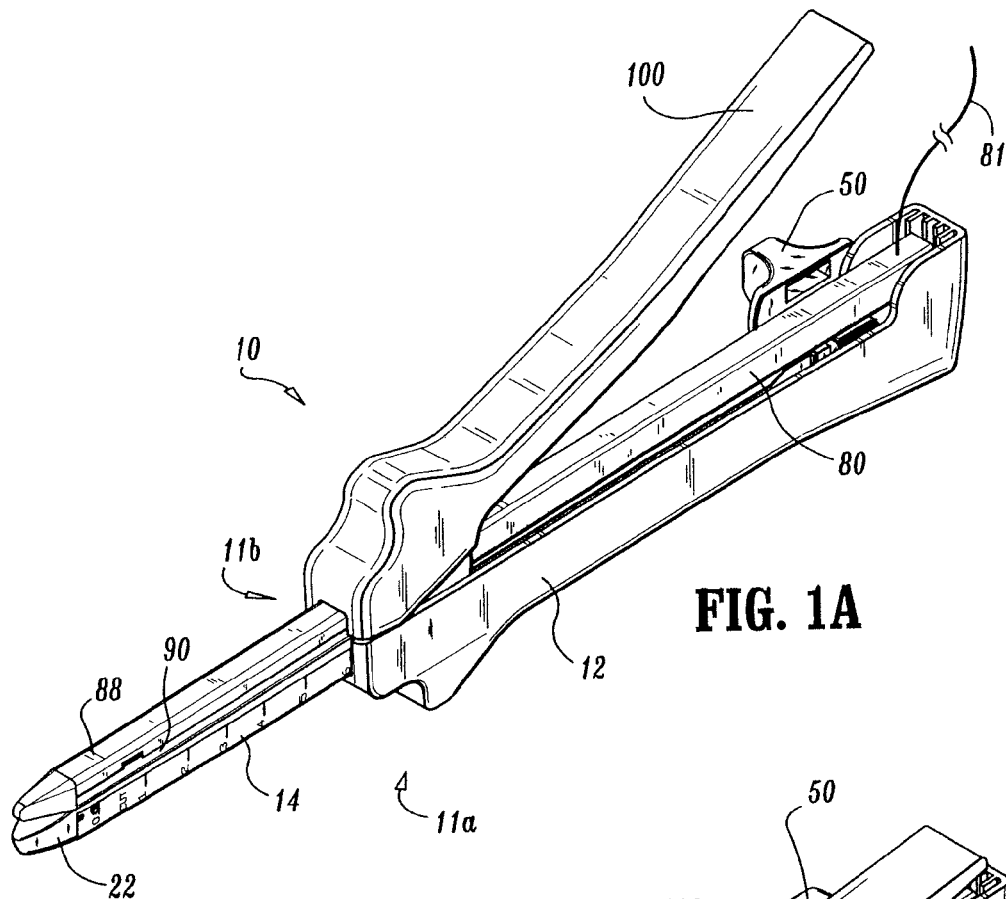
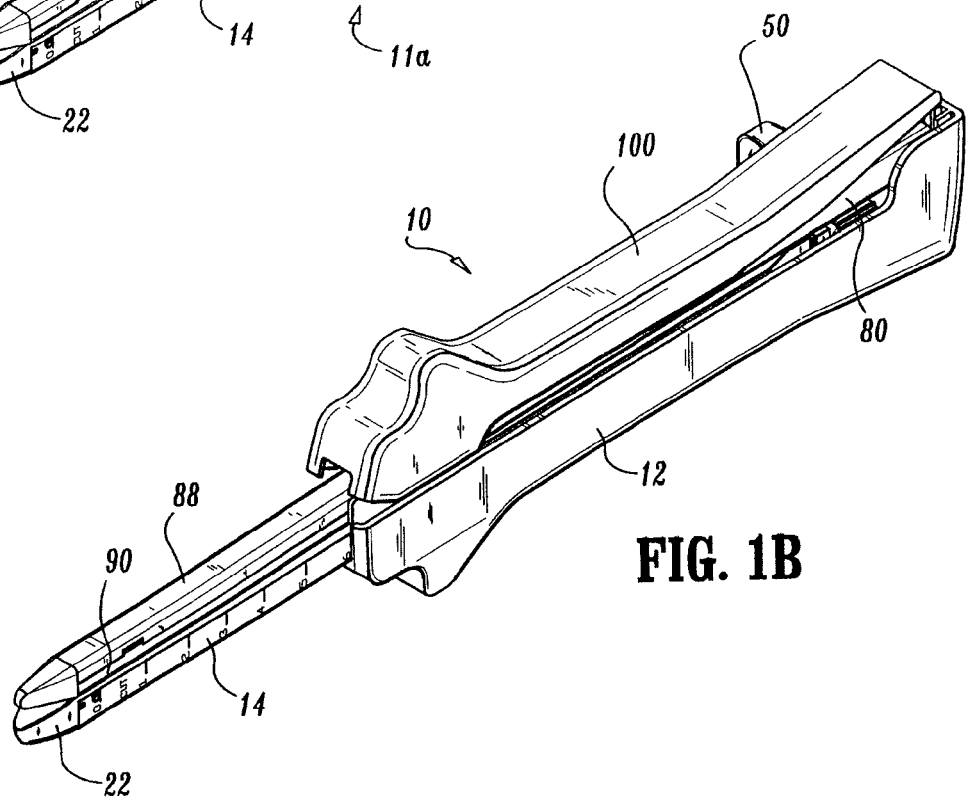

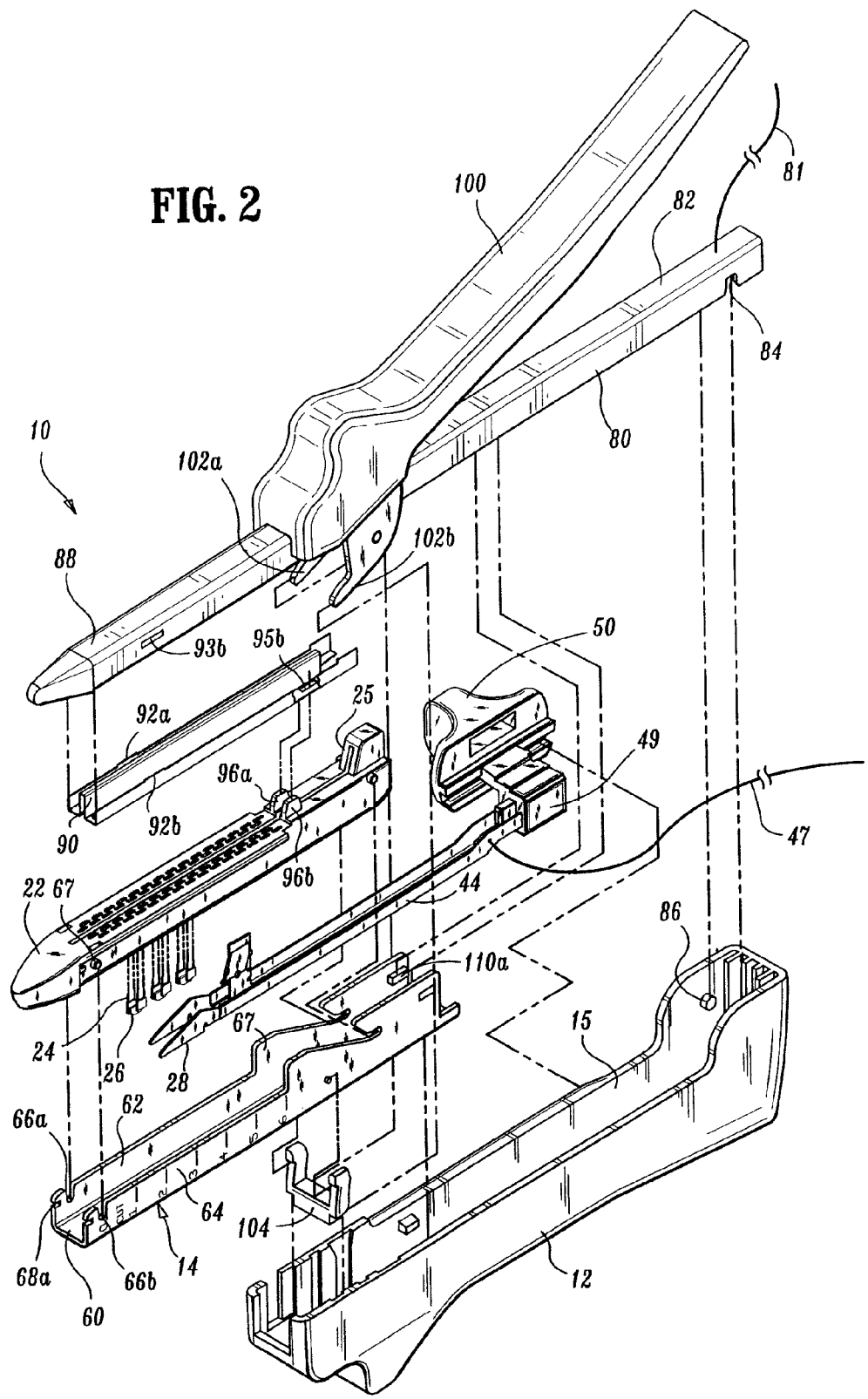

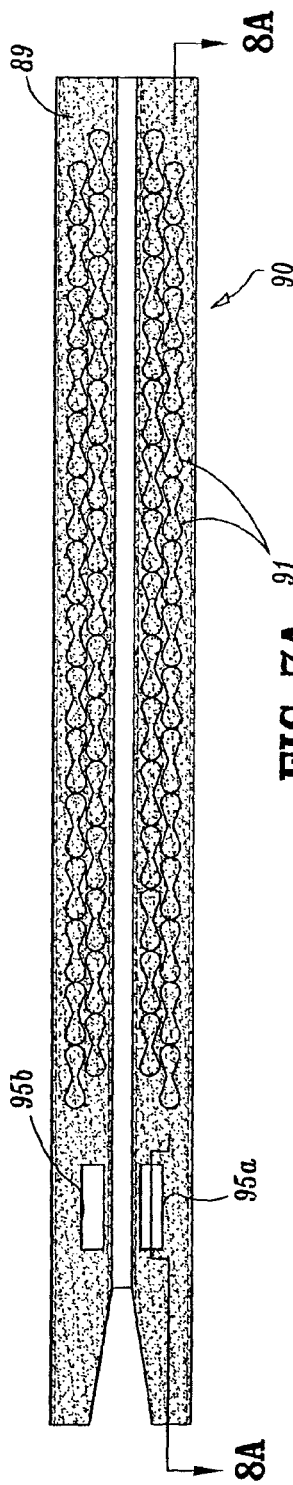
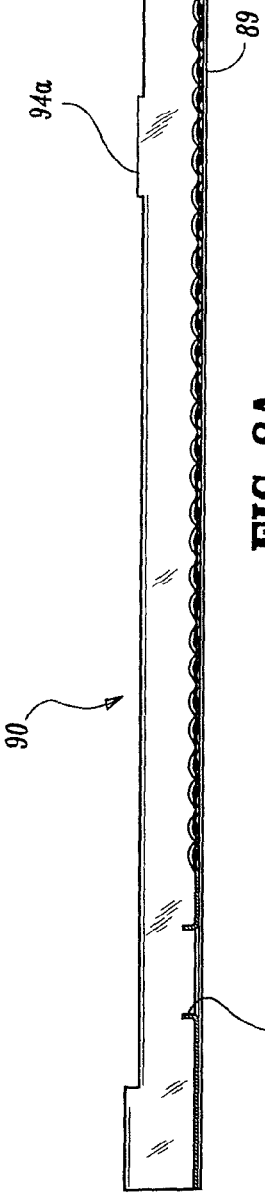
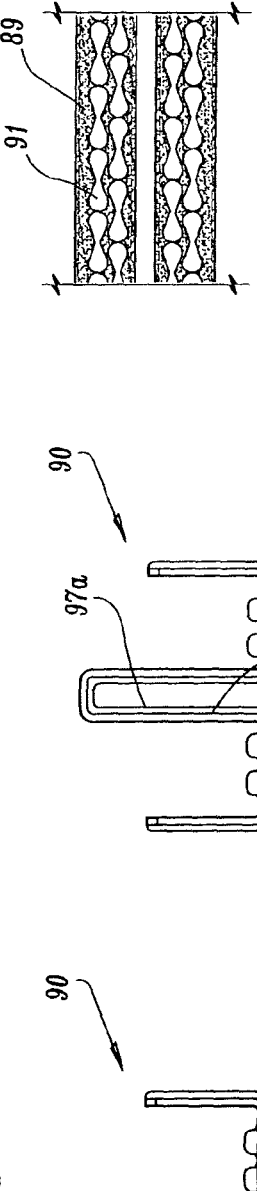
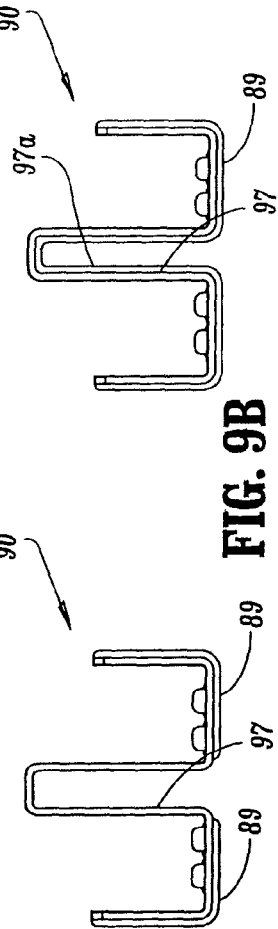

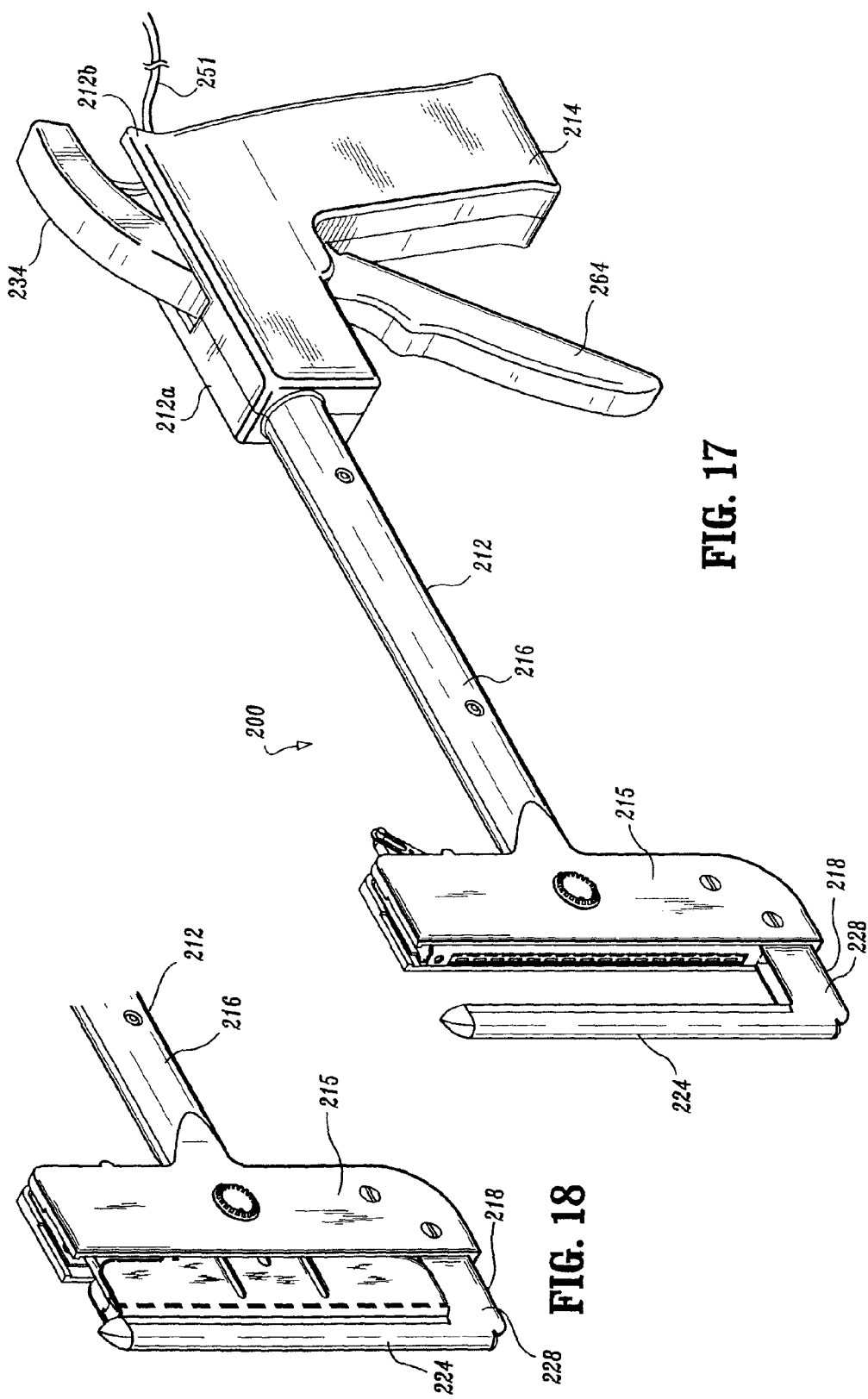

ELECTROSURGICAL STAPLING APPARATUS

CROSS-REFERENCE TO RELATED APPLICATIONS

This application is a continuation of U.S. application Ser. No. 11/707,818 filed Feb. 16, 2007, now U.S. Pat. No. 7,559,453, which is a continuation of U.S. application Ser. No. 10/513,435 filed Nov. 1, 2004, now U.S. Pat. No. 7,207,471, which claims priority under 35 U.S.C. 371 from International application No. PCT/US2003/014520 filed May 9, 2003, which claims benefit of U.S. Provisional application No. 60/379,961 filed May 10, 2002. This application is also a continuation of U.S. application Ser. No. 12/363,827 filed Feb. 2, 2009. The disclosures of each of the above-identified applications are hereby incorporated by reference in their entirety.

FIELD OF THE INVENTION

This invention relates to surgical staplers, and more particularly, to an electrosurgical stapling apparatus for sequentially applying a plurality of surgical fasteners to body tissue.

BACKGROUND OF THE INVENTION

Surgical procedures requiring cutting of tissue can result in bleeding at the site of the cutting. Various techniques have been adapted to control bleeding with varying degrees of success such as, for example, suturing, applying clips to blood vessels, and using surgical fasteners, as well as electrocautery and other tissue heating techniques.

Surgical devices using surgical fasteners entail grasping or clamping tissue between opposing jaw structure and then joining the tissue by employing the surgical fasteners. These devices are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of staples arranged in at least two lateral rows while the other member comprises an anvil which defines a surface for forming the staple legs as the fasteners are driven from the cartridge. Where two part fasteners are used, this member carries the mating part, e.g. the receiver, to the fasteners driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. Nos. 3,079,606 and 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929, and 5,156,614.

Electrocautery devices are preferred in certain surgical procedures for effecting improved hemostasis by heating tissue and blood vessels using thermogenic energy, preferably radiofrequency energy, to cause coagulation or cauterization. Monopolar devices utilize one electrode associated with a cutting or cauterizing instrument and a remote return electrode, usually adhered externally to the patient. Bipolar instruments utilize two electrodes and the cauterizing current is generally limited to tissue between the two electrodes of a tissue treating portion (e.g., end effector) of an instrument.

It would be desirable to have electrosurgical stapling devices combining the structural and functional aspects of stapling instruments and electrocautery devices to provide improved hemostasis by using thermogenic energy to cause coagulation or cauterization and surgical fasteners to staple the tissue, either before, during or after the use of thermogenic energy.

Therefore, it is an aspect of the invention to provide an electrosurgical stapling apparatus which uses thermogenic energy and staples for providing hemostasis, tissue joining or welding, and also strengthens tissue in proximity to a staple line and provides hemostasis along the staple line to reduce or prevent staple line bleeding.

SUMMARY

An electrosurgical stapling apparatus is disclosed which uses thermogenic energy, preferably radiofrequency energy, as well as surgical fasteners or staples for strengthening tissue, providing hemostasis, tissue joining or welding. The thermogenic energy also strengthens tissue in proximity to a staple line and knife cut line and provides hemostasis along the staple and cut lines formed by the staples and a knife blade during surgical stapling. The use of thermogenic energy provides short-term hemostasis and sealing, and reduces or prevents staple line and cut line bleeding, while the stapling features provide short and long-term tissue strength and hemostasis.

Staple line bleeding is reduced or prevented by the apparatus by thermogenically energizing the staples before, during, and/or after a stapling procedure to increase the temperature of the staples to a temperature sufficient to cauterize tissue. Hence, as the staples penetrate the tissue, the tissue is cauterized, thereby reducing or preventing staple line bleeding.

Since staple line bleeding is reduced or prevented, the apparatus of the present invention makes it possible to extend the applicable range of specific staple sizes to include thinner, thicker and highly vascularized tissue. Accordingly, large-size staples can be used, for example, with the apparatus of the present invention to join thin, highly vascularized tissue.

One embodiment of the apparatus is an improved surgical stapler including a first body portion defining a surface against which a plurality of surgical staples are driven when ejected from a second body portion by an actuation member, which can be a sled, mounted to translate through the first body portion. The second body portion houses the plurality of surgical staples. The improved surgical stapler further includes at least one conductive member supported by the first body portion for sequentially applying thermogenic energy to the plurality of surgical staples for providing hemostasis along at least one staple line during surgical stapling.

The type of thermogenic energy applied to the surgical staples can be radiofrequency, pure thermal, or resistive heating. The at least one conductive member can be a metallic anvil, where the surface is an outer surface of the metallic anvil. The surface includes a plurality of staple-receiving recesses and preferably is coated with an insulation material. The insulation material can be configured for being partially removable by staples when driven against the first body portion during surgical stapling for energizing the surgical staples via the at least one conductive member. Alternatively, the plurality of staple-receiving recesses are not coated with the insulation material. The insulation material can be selected from the group consisting of Teflon and plastics.

The actuation member or sled can include a knife blade that can be supported by or fastened to an upstanding flange. The knife blade can traverse through a knife slot, cavity, track, etc. formed in the first body portion. At least one other conductive member can be used to apply thermogenic energy to the knife blade during surgical stapling to cauterize tissue along at least one cut line. The at least one other conductive member can be a surface which defines the knife slot, cavity, track, etc. formed in the first body portion. The at least one conductive member energizes the plurality of surgical staples via the surface defined by the first body portion for providing hemostasis along at least one staple line during surgical stapling.

Another embodiment of the apparatus includes a first body portion supporting a metallic anvil plate which defines a fastener forming surface and a second body portion configured to releasably mate with the first body portion. In the detailed description which follows, the first and second body portions of the apparatus are also referred to as the "anvil half-section" and "cartridge half-section", respectively.

The second body portion can include a disposable loading unit, and either can include a cartridge defining a plurality of slots and a tissue contacting surface, a plurality of surgical fasteners disposed in the slots of the cartridge, and a plurality of ejectors or pushers positioned adjacent the surgical fasteners. The surgical fasteners and the ejectors preferably are fabricated from a metallic alloy or other type of material capable carrying thermogenic energy.

A metallic actuator or actuation sled can be provided in the disposable loading unit is positioned and configured to enter and translate through the cartridge to sequentially interact with the pushers. The actuator is energized or electrified by radiofrequency energy generated by an external radiofrequency generator or other thermogenic generator for energizing the surgical fasteners via the pushers. The external generator is connected to the actuator or actuation sled via at least one wire for energizing the actuator upon activation of the external generator.

The apparatus further includes an elongated actuation member mounted for longitudinal movement within the second body portion or cartridge and releasably engagable with the actuator or actuation sled, whereby longitudinal movement of the actuation member causes the actuator to interact with the ejectors, driving the surgical fasteners from the cartridge to be formed against the anvil plate.

The first body portion preferably includes an elongate anvil support member and a pivoting lever handle. The anvil plate is preferably formed separate from the anvil support member and includes a plurality of staple forming pockets defining the anvil forming surface. The anvil plate also includes means for engaging the anvil support member during assembly of the apparatus to securely fasten the anvil plate to the support member. The anvil plate is connected via at least one return wire to the external generator to behave as a return electrode with respect to the actuator of the disposable loading unit and the surgical fasteners for bipolar operation.

A notched area is defined adjacent a proximal end of the anvil support member and correspondingly positioned detents are formed adjacent a proximal end of the second body portion. The notched area and the detents cooperate to facilitate relative pivotal movement of the first and second body portions when they are mated with one another.

Preferably, a pair of upstanding flanges are formed on the disposable loading unit proximal of the tissue contacting surface thereof. The flanges define a structural tissue stop to limit the movement of body tissue. The flanges are also dimensioned to engage a pair of corresponding apertures formed in the anvil plate to maintain the first and second body portions in alignment with one another when the apparatus is in a closed or clamped position.

The actuator of the disposable loading unit is preferably monolithically formed from a planar piece of sheet metal during a stamping process and includes a planar base and a pair of upstanding parallel cam wedges. An upturned flange is formed at a distal end of the actuation member for releasably engaging a complementary slot formed in the base of the actuator. The actuator preferably further includes an upstanding support flange to which a knife blade is fastened. The knife blade is provided to form an incision in the stapled body tissue while also being energized by thermogenic energy via the actuator for improved hemostasis. It is contemplated to connect the knife blade to the actuator via a non-conductive member, e.g., a plastic member, if heating of the knife blade is not desired, or to simply remove the knife blade from the upstanding support.

A retaining channel depends from a distal end of the second body portion for supporting the disposable loading unit. Preferably, the disposable loading unit and the retaining channel include complementary engagement structures for releasably securing the disposable loading unit in the retaining channel. Opposed bearing structures are formed in the retaining channel at a proximal end thereof for abutting the anvil support beam when body tissue is clamped between the anvil plate and the tissue contacting surface of the cartridge. The bearing structures serve to inhibit the anvil support beam from bending as a result of the compressive forces generated during clamping.

The thermogenic energy can be monopolar or bipolar radiofrequency, pure thermal, and resistive heating, and is applied to the stapling apparatus to energize or heat the staples either directly and/or via one or more conductive members before, during, and/or after the apparatus has stapled, cauterized, and/or cut tissue.

Still, another embodiment of the invention includes a surgical stapler including a first body portion supporting an anvil which defines a fastener forming surface; a second body portion configured to releasably mate with the first body portion; and an elongated actuation member mounted for longitudinal movement within a cartridge, which can be a disposable loading unit, supported by the second body portion. The elongated actuation member has an engagement member releasably coupled to engagement structure to enable pushing and pulling of the actuation member to effect movement of the actuation member in proximal and distal directions, respectively. The surgical stapler further includes at least one conductive member for applying thermogenic energy to the surgical fasteners via the engagement member for providing hemostasis along at least one staple line during surgical stapling.

The cartridge defines a plurality of slots and a tissue contacting surface; a plurality of surgical fasteners disposed in the slots of the cartridge; a plurality of ejectors positioned adjacent the surgical fasteners; and an actuator configured to translate through the cartridge to sequentially interact with the ejectors. The type of thermogenic energy applied to the surgical fasteners can be selected radiofrequency, pure thermal, or resistive heating.

The first body portion can include an elongate anvil support member and a pivoting lever handle for approximating the first and second body portions. At least one return wire can be connected to the elongate anvil support member for bipolar operation with respect to the at least one conductive member. The anvil can include an anvil plate formed separate from the first body portion and includes a plurality of staple forming pockets. The first body portion has an anvil support member and the anvil plate includes structure for engaging the anvil support member during assembly of the surgical stapler to securely fasten the anvil plate to the anvil support member. A notched area can be defined adjacent a proximal end of the anvil support member and correspondingly positioned detents can be formed adjacent a proximal end of the second body portion. The notched area and the detents cooperate to facilitate relative pivotal movement of the first and second body portions.

A pair of upstanding flanges can be formed on the disposable loading unit proximal of a tissue contacting surface thereof. The pair of upstanding flanges are dimensioned to engage a pair of corresponding apertures formed in the anvil plate to maintain the first and second body portions in alignment with the surgical stapler in a closed position.

The actuator can include a planar base portion and/or a pair of upstanding parallel cam wedges. An upturned flange is formed at a distal end of the actuation member for releasably engaging a complementary slot formed in the base portion of the actuator. The actuator can be monolithically formed.

The surgical stapler can include a knife blade, and the at least one conductive member further applies thermogenic energy to the knife blade during surgical stapling. The knife blade can be carried by the actuator and the at least one conductive member can further apply thermogenic energy to the knife blade during surgical stapling.

A retaining channel can depend from a distal end of the second body portion for supporting the disposable loading unit. The retaining channel can include engagement structure for releasably securing the disposable loading unit in the retaining channel. Opposed bearing structures can be formed in the retaining channel adjacent a proximal end thereof for abutting the anvil support beam when body tissue is clamped between the anvil plate and the tissue contacting surface of the cartridge.

The surgical stapler can include a firing knob extending from the second body portion for sliding movement in a longitudinal direction. The elongated actuation member can be operatively connected at a proximal end to the firing knob. The staple actuator can include a planar base portion, a pair of upstanding parallel cam wedges disposed in a staggered orientation and an upstanding blade support flange to which a knife blade is fastened. The staple actuator can include an upturned flange formed at a distal end of the elongated actuator for releasably engaging a complementary slot formed in the base portion of the staple actuator.

Still in another embodiment, a surgical stapler for applying a plurality of surgical fasteners to body tissue is provided. The surgical stapler includes a first body portion having an anvil which defines a fastener forming surface against which surgical fasteners are driven; a second body portion having an elongate retention channel; and a cartridge and/or a disposable loading unit supported in the elongate retention channel of the second body portion. The cartridge defines a plurality of slots and a tissue contacting surface; a plurality of surgical fasteners disposed in the slots of the cartridge; a plurality of ejectors positioned adjacent the surgical fasteners; and an actuator configured to enter and translate through the cartridge to sequentially interact with the ejectors. The surgical stapler further includes at least one conductive member supported by the second body portion for applying thermogenic energy to the plurality of surgical fasteners for strengthening tissue in proximity to at least one staple line and/or for providing hemostasis along the at least one staple line during surgical stapling.

The type of thermogenic energy applied to the surgical fasteners can be radiofrequency, pure thermal, or resistive heating. The actuator can include two upstanding cam wedges, an upstanding flange positioned between the cam wedges, and a knife blade attached to the upstanding flange. The surgical stapler can include an elongated actuation member mounted for longitudinal movement within the second body portion and operatively associated with the actuator such that longitudinal movement of the actuation member causes the actuator to interact with the ejectors to drive the surgical fasteners from the cartridge to be formed against the anvil.

In the alternative, the surgical fasteners are energized via the anvil. In this embodiment, the anvil surface is energized which in turn energizes the surgical staples as they contact the anvil surface during surgical stapling. It is preferred to coat the metallic anvil surface with an insulating material, such as Teflon, soft plastics (PVC), etc., to prevent the energized anvil surface from energizing tissue which is contacted by the anvil surface.

During a surgical stapling procedure, as the staples are ejected against the anvil surface, the staples scratch off the insulation coating and make contact with the metallic anvil surface, thus becoming energized. In the alternative, the staple-forming pockets of the anvil surface are not coated, such that the staples do not need to scratch off the insulation coating. The rest of the anvil surface, however, is insulated. Further, it is preferred for the anvil to energize the knife blade as the knife blade traverses through the disposable loading unit by making contact with the knife blade, either directly or indirectly.

A method is further disclosed for providing hemostasis along at least one staple line during surgical stapling. The method includes the steps of providing a plurality of surgical fasteners; and applying thermogenic energy to an anvil surface against which the plurality of surgical fasteners are driven when ejected by a staple actuator for energizing the plurality of surgical fasteners via the anvil surface. The method can further comprise the step of applying thermogenic energy to a knife blade during surgical stapling, either via the anvil surface and/or some other structure, such as a cartridge housing the plurality of surgical fasteners. The thermogenic energy can be applied to the surgical fasteners via the anvil surface sequentially, and the type of thermogenic energy applied to the surgical fasteners via the anvil surface can be radiofrequency, pure thermal, or resistive heating. As discussed above, the entire anvil surface or the entire anvil surface, except for the pockets configured to engage the surgical fasteners, is preferably insulated to prevent the anvil surface from energizing tissue.

During surgical stapling, the surgical fasteners are ejected and scratch the material insulating the anvil surface (if the pockets are coated), thereby becoming energized. If the pockets are not coated, the surgical fasteners make contact with the metallic anvil surface and become energized.

Further features of the surgical apparatus of the invention will become more readily apparent to those skilled in the art from the following detailed description of the apparatus taken in conjunction with the drawings.

BRIEF DESCRIPTION OF THE DRAWINGS

Various embodiments of the surgical stapling apparatus of the invention will be described hereinbelow with reference to the drawings wherein:

FIG. 1A is a perspective view of an electrosurgical stapling apparatus constructed in accordance with a preferred embodiment with the clamping handle thereof disposed in an upright open position;

FIG. 1B is a perspective view of the electrosurgical stapling apparatus illustrated in FIG. 1A with the clamping handle disposed in a closed position;

FIG. 2 is an exploded perspective view of the electrosurgical stapling apparatus of FIGS. 1A and 1B;

FIG. 7A is a plan view of the preformed anvil plate which is mounted to the anvil support beam of the upper body portion of the electrosurgical stapling apparatus shown in FIGS. 1A and 1B having an insulation material applied thereon;

FIG. 8A is a cross-sectional view of the preformed anvil plate taken along line 8-8 of FIG. 7A;

FIG. 9A is a front end view of the preformed anvil plate illustrated in FIGS. 7 and 8 having an insulation material applied thereon;

FIG. 9B is a front end view of the preformed anvil plate illustrated in FIGS. 7 and 8 having an insulation material applied thereon;

FIG. 9C is a top view of the preformed anvil plate illustrated in FIGS. 7A and 8A having an insulation material applied thereon except within staple-forming cups;

FIG. 17 is a perspective view of an electrosurgical stapling apparatus constructed in accordance with another preferred embodiment;

FIG. 18 is a perspective view of the distal end of the embodiment of the disclosure shown in FIG. 17 with the cartridge assembly in an advanced position;

DETAILED DESCRIPTION OF PREFERRED EMBODIMENTS

Figure 3:
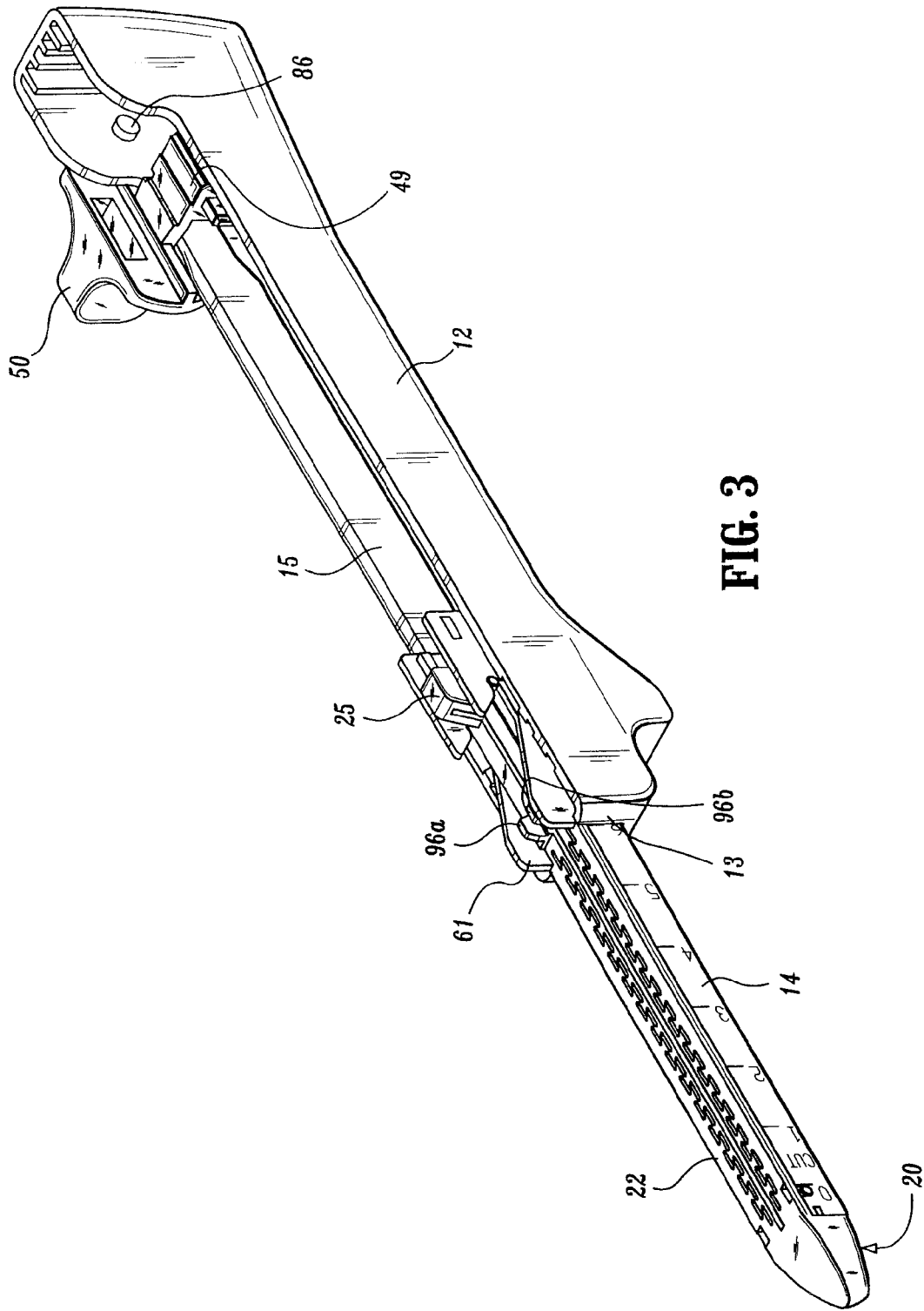
FIG. 3 is a perspective view of the lower body portion of the electrosurgical stapling apparatus of FIGS. 1A and 1B.

The present invention provides a stapling apparatus which uses thermogenic energy, preferably radiofrequency energy generated by an external radiofrequency generator, as well as surgical fasteners or staples for strengthening tissue, providing hemostasis, tissue joining or welding. The thermogenic energy also strengthens tissue in proximity to a staple line and knife cut line and provides hemostasis along the staple and cut lines formed by the staples and a knife blade during surgical stapling. The use of thermogenic energy provides short-term hemostasis and sealing, and reduces or prevents staple line and cut line bleeding, while the stapling features provide short and long-term tissue strength and hemostasis.

Staple line bleeding is reduced or prevented by the apparatus, by thermogenically energizing the staples before, during, and/or after a stapling procedure to increase the temperature of the staples to a temperature sufficient to cauterize tissue. Hence, as the staples penetrate the tissue, the staples cauterize the tissue, including blood vessels, to reduce or prevent staple line bleeding.

Since staple line bleeding is reduced or prevented, the apparatus of the present invention makes it possible to extend the applicable range of specific staple sizes to include thinner, thicker and highly vascularized tissue. Accordingly, large-size staples can be used, for example, with the apparatus of the present invention to join thin, highly vascularized tissue. It is also provided that the present invention further reduces or prevents knife cut line bleeding by energizing a knife blade for cauterizing the tissue while it is being cut.

In the drawings and in the following description, the term "proximal", as is traditional, will refer to the end of the apparatus which is closer to the operator, while the term "distal" will refer to the end of the apparatus which is further from the operator.

Referring now to the drawings wherein like reference numerals identify similar structural elements, there is illustrated in FIGS. 1A and 1B an electrosurgical stapling apparatus constructed in accordance with a preferred embodiment and designated generally by reference numeral 10 which includes a cartridge half-section 11a and an anvil half-section 11b. As will become readily apparent to those having ordinary skill in the art, stapling apparatus 10 is constructed in such a manner so as to substantially reduce the costs associated with its fabrication and assembly as compared to prior art linear staplers.

Figure 4A:
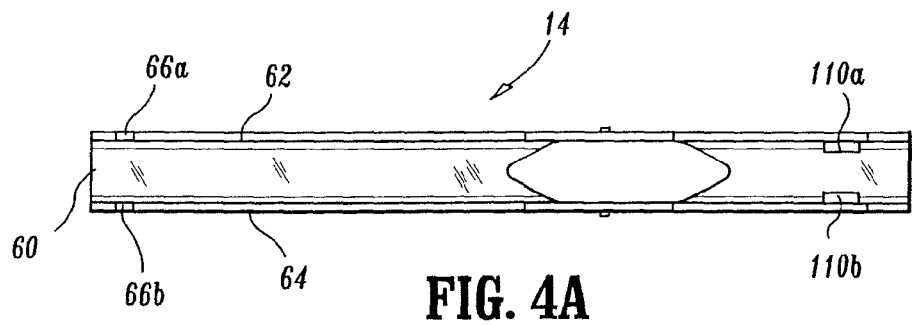
FIG. 4A is a top plan view of the retention channel of the electrosurgical stapling apparatus of FIGS. 1A and 1B.
Figure 4B:
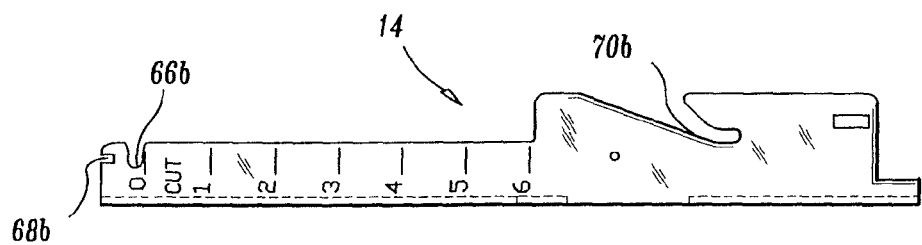
FIG. 4B is a side elevational view of the retention channel shown in FIG. 4A.
Figure 4C:
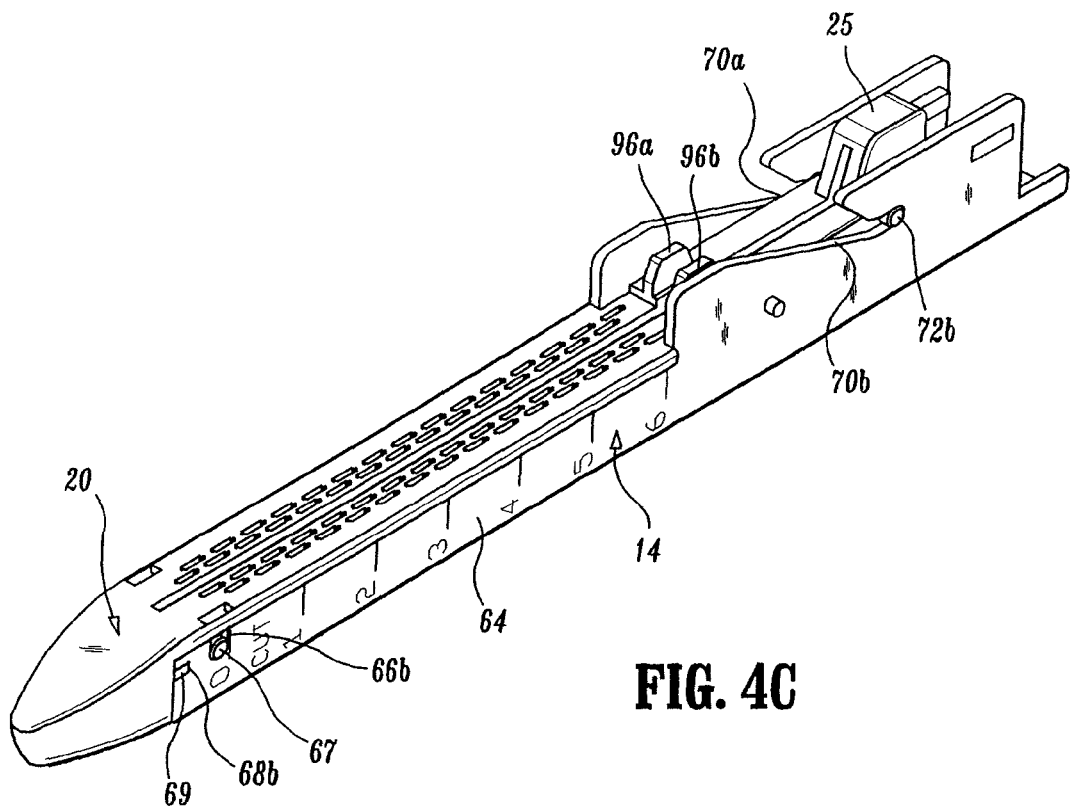
FIG. 4C is a perspective view of the retention channel of FIGS. 4A and 4B with the disposable loading unit retained therein.

Referring to FIGS. 2 and 3, stapling apparatus 10 includes a body portion 12 defining a handle for grasping and supporting the device. A retaining channel 14 is mounted in the interior cavity 15 of body portion 12 adjacent the distal end thereof. Retaining channel 14 is dimensioned and configured to support a disposable loading unit 20, as illustrated in FIG. 4C.

Figure 5A:
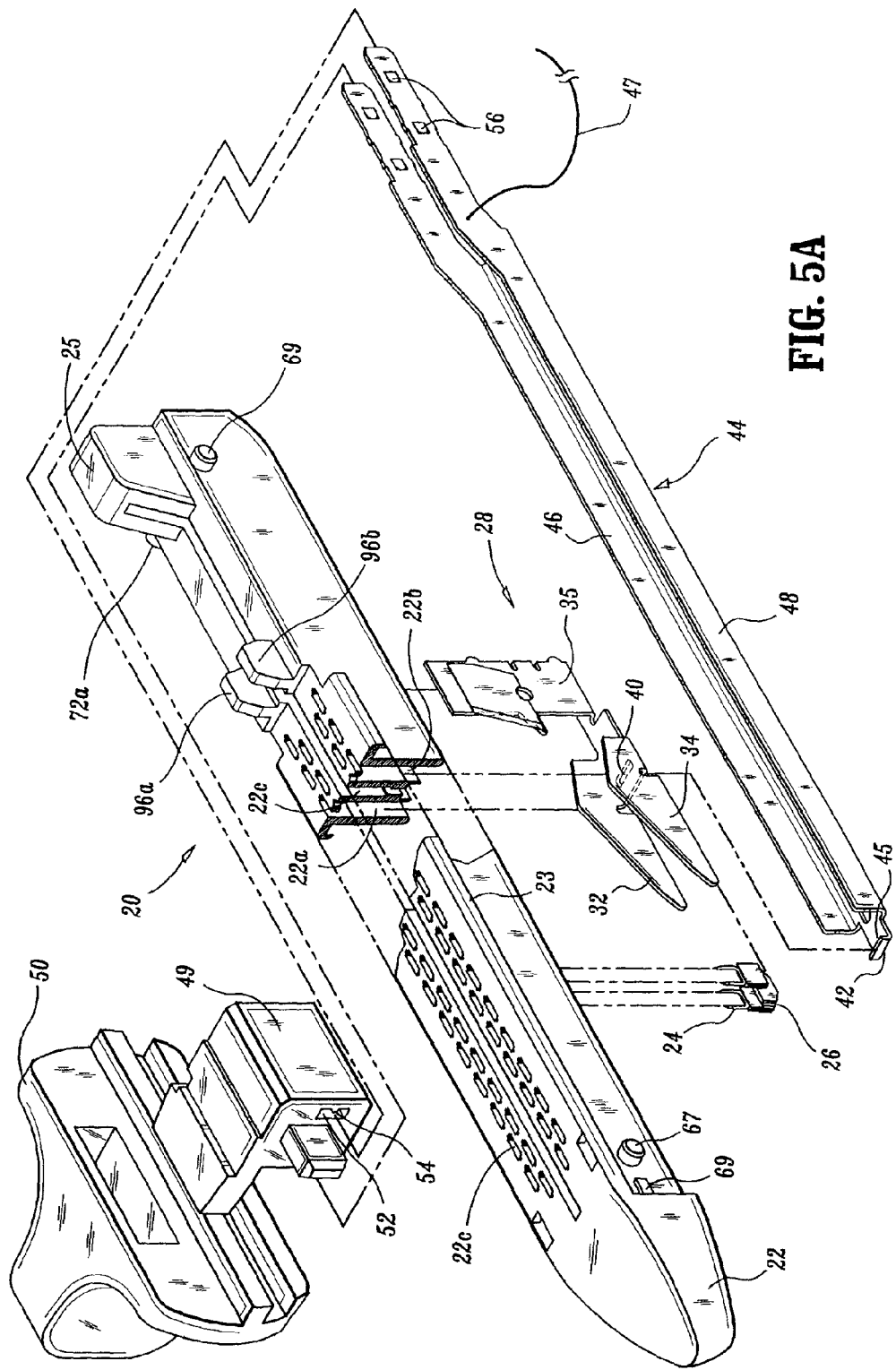
FIG. 5A is an enlarged perspective view, with parts separated for ease of illustration, of the disposable loading unit and actuation assembly of the electrosurgical stapling apparatus of the subject application.
Figure 5B:
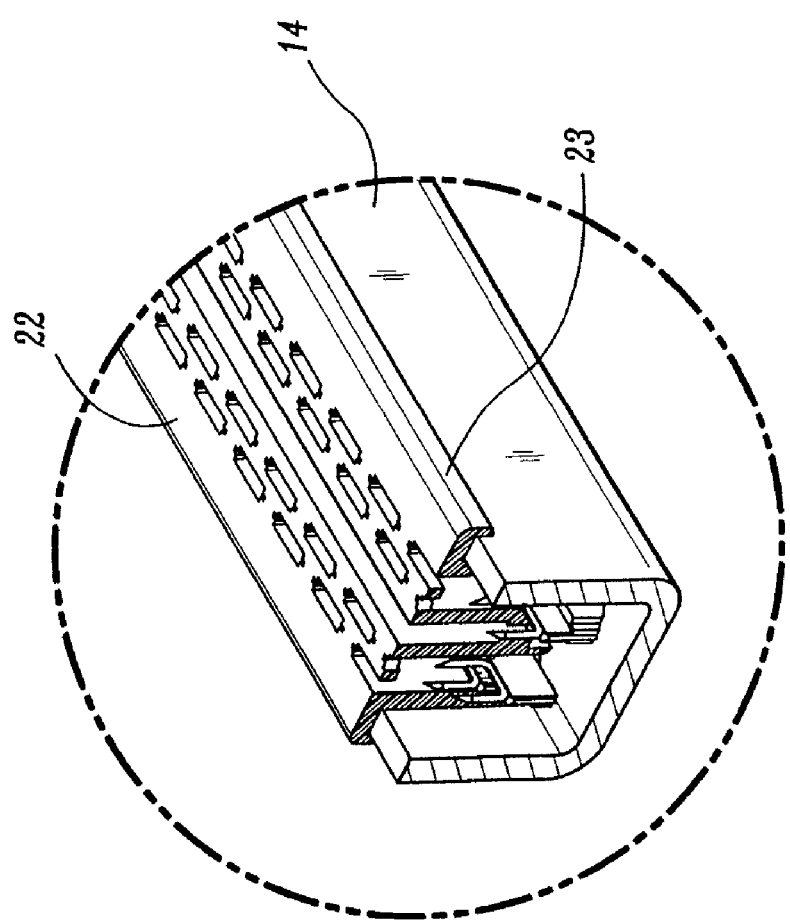
FIG. 5B is a cross-sectional view showing the engagement of the cartridge lip and the retention channel.

As shown in FIG. 5A, the disposable loading unit 20 includes a cartridge 22 having a plurality of slots 22c which support a corresponding number of metallic surgical staples 24, a plurality of metallic staple pushers or ejectors 26 adapted and configured to eject the staples 24 from slots 22c when acted upon by a staple driving force, and an actuation sled or actuator 28 which is mounted to translate through cartridge 22 in a longitudinal direction to transmit a staple driving force to ejectors 26 while simultaneously energizing ejectors 26 by thermogenic energy generated by an external generator, preferably a radiofrequency generator. The cartridge 22 is preferably composed of liquid crystal polymer material; although other materials are contemplated. The cartridge 22 has a lip 23 which engages the retention channel 14 to prevent inward rotation of the cartridge (see FIG. 5B).

Figure 6A:
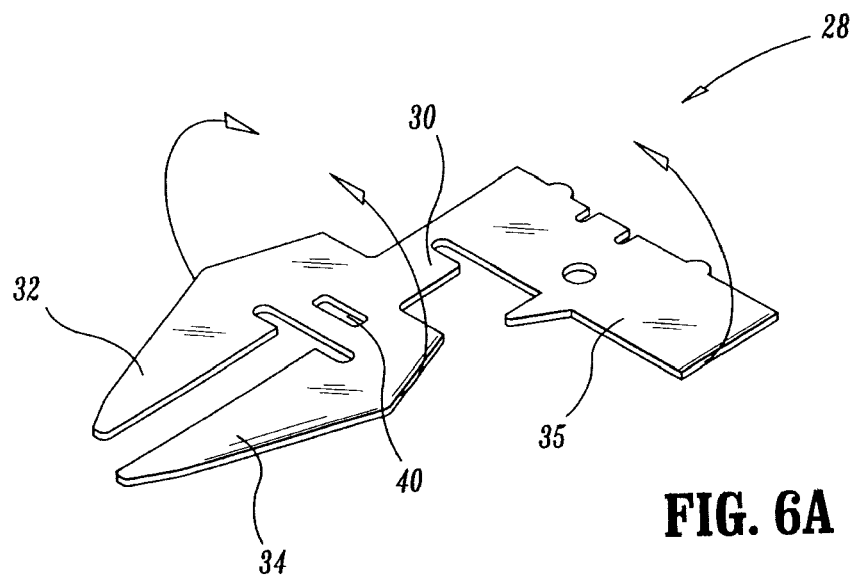
FIG. 6A is a perspective view of the actuation sled of the disposable loading unit shown in FIG. 5A in a pre-formed condition.
Figure 6B:
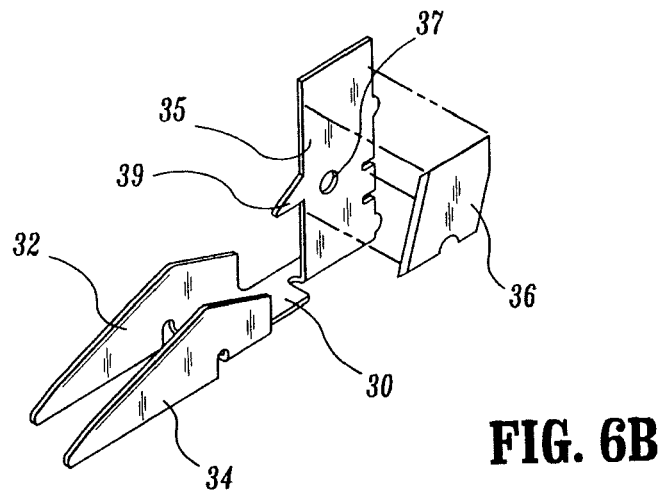
FIG. 6B is a perspective view of the actuation sled shown in FIG. 6A in a formed condition with the knife blade separated therefrom for illustrative purposes.
Figure 6C:
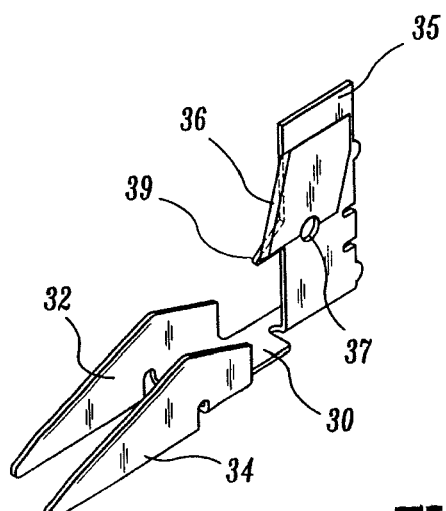
FIG. 6C is a perspective view of the formed actuation sled shown in FIG. 6B with the knife blade mounted to the blade support portion thereof.

As best seen in FIG. 6A, actuation sled 28 is preferably monolithically formed from a single piece of sheet metal or a similar conductive material which is folded into the desired structural configuration shown in FIG. 6C. In this configuration, actuation sled 28 defines a base portion 30, two upstanding cam wedges 32 and 34, and an upstanding shank 35 which supports a knife blade 36. Knife blade 36 is preferably spot welded to shank 35, although other known fastening methods may be employed, for transferring thermogenic energy to knife blade 36 via actuation sled 28. It is contemplated to connect knife blade 36 to actuation sled 28 via a non-conductive member, e.g., a plastic member, if heating of knife blade 36 is not desired, or to simply remove knife blade 36 from upstanding shank 35.

As illustrated in FIG. 6B, a weldment port 37 and a winglet 39 are provided to facilitate the proper alignment and cohesion of knife blade 36 to shank 35 during fabrication. Cam wedges 32 and 34 are staggered with respect to one another so that one leads the other throughout the sled's translation through cartridge 22. In doing so, the staple driving forces within cartridge 22 remain balanced during a staple driving operation. Longitudinal slots 22a and 22b accommodate the longitudinal translation of cam wedges 32 and 34, while slot 22c accommodates the longitudinal translation of shank 35 (see FIG. 5A). Although illustrated with a knife, it is also contemplated that the apparatus can be provided without a knife blade to staple tissue without making an incision.

The base portion 30 of actuation sled 28 has a transverse slot 40 defined therein which is dimensioned and configured to releasably retain an upturned flange 42 formed at the distal end of elongated actuation channel 44 (FIG. 5A). When the disposable loading unit 20 is placed into retaining channel 14 and actuation sled 28 is disposed in its proximal-most position, flange 42 releasably engages slot 40. Thus, movement of actuation channel 44 moves actuation sled 28.

As shown in FIG. 5A, at least one wire 47 is connected to actuation channel 44 and to an external generator (not shown), preferably a radiofrequency generator, for providing thermogenic energy to actuation channel 44 to energize or heat the same. The energizing of actuation channel 44 causes the energizing of actuation sled 28 via upturned flange 42, thereby also energizing cam wedges 32, 34. Cam wedges 32, 34 in turn energize staple pushers 26 which in turn energize staples 24 (see FIGS. 15 and 16). After a stapling operation, when disposable loading unit 20 is removed from the retaining channel, flange 42 is easily disengaged from slot 40.

With continued reference to FIG. 5A, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam projects rearwardly to engage a non-conductive mounting block 49 that is associated with firing knob 50. A pair of slots 52 (only one of which is shown) are formed in mounting block 49 for receiving the proximal end of each of the upstanding beams 46, 48 of actuation channel 44 and the slots are provided with detents 54 for engaging apertures 56 in the beam ends to lockingly retain beams 46, 48 in mounting block 49. In use, longitudinal movement of firing knob 50 causes corresponding longitudinal translation of actuation channel 44 and actuation sled 28.

Referring to FIGS. 2 and 4C, retention channel 14 includes a base portion 60 and two upstanding parallel walls 62 and 64. Numerical indicia is imprinted on the walls 62, 64 of retention channel 14 to indicate the length of the staple line. Retention structures are provided at the distal end of each of the walls 62, 64 to engage corresponding structures provided on the disposable loading unit 20. In particular, notches 66a and 66b are provided for engaging corresponding protuberances, such as protuberance 67, and slots 68a and 68b are provided for engaging corresponding detents, such as detent 69. These structures inhibit lateral, longitudinal and perpendicular shifting of the cartridge 22 (and disposable loading unit 20) within the retaining channel 14. Ramped engagement slots 70a and 70b are also defined in the opposed walls of retention channel 14 for interacting with a pair of opposed protuberances 72a and 72b (FIG. 5A) to guide the disposable loading unit 20 into retention channel 14 when loaded into the electrosurgical stapling apparatus 10.

Referring again to FIG. 2, the electrosurgical stapling apparatus 10 further includes an elongate anvil support beam 80 which has a generally U-shaped cross-sectional configuration. Anvil support beam 80 and its associated structures are all conductive, except where otherwise noted, and are also referred to herein as the "anvil half-section". Distal end portion 88 of the anvil support beam 80 in one embodiment is tapered in height "h" in a distal direction to provide additional support and reduce deflection during a staple firing operation. Proximal end portion 82 of support beam 80 has a notched area 84 for engaging a pair of corresponding detents 86 (only one of which is shown), which extend into the cavity 15 of body portion 12 adjacent the proximal end thereof. Detents 86 are engaged when cartridge half-section 11a and anvil half-section 11b are mated with one another. Distal end portion 88 of anvil support beam 80 is configured to support a preformed anvil plate 90 against which staples 24 are driven and formed during a stapling procedure.

Figure 7:
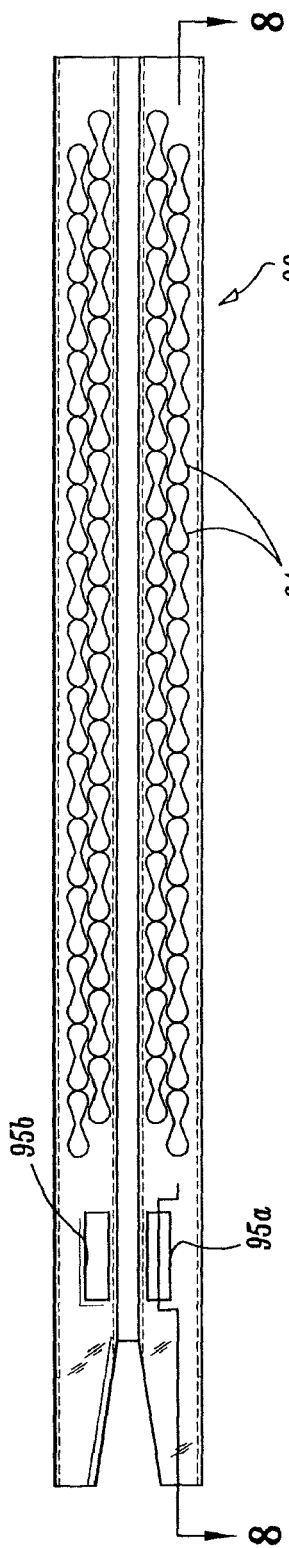
FIG. 7 is a plan view of the preformed anvil plate which is mounted to the anvil support beam of the upper body portion of the electrosurgical stapling apparatus shown in FIGS. 1A and 1B.
Figure 8:
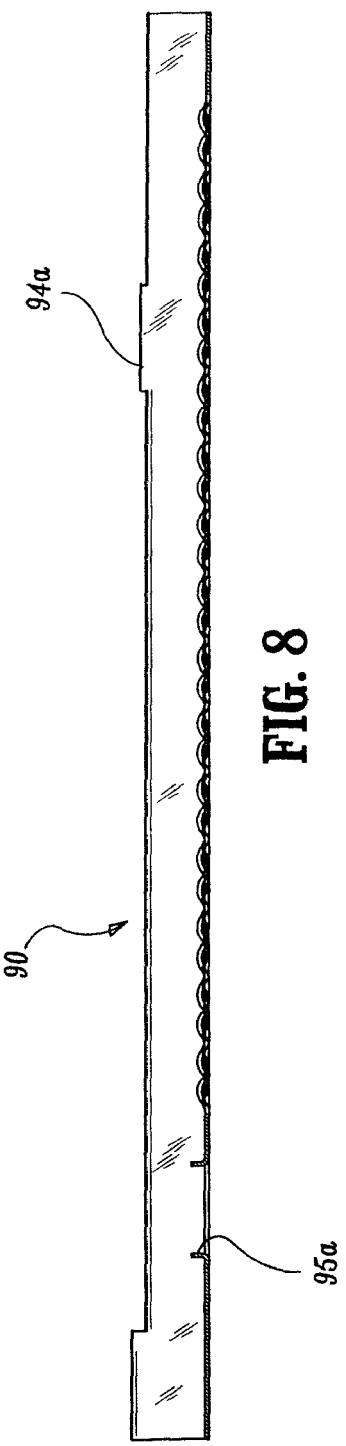
FIG. 8 is a cross-sectional view of the preformed anvil plate taken along line 8-8 of FIG. 7.
Figure 9:
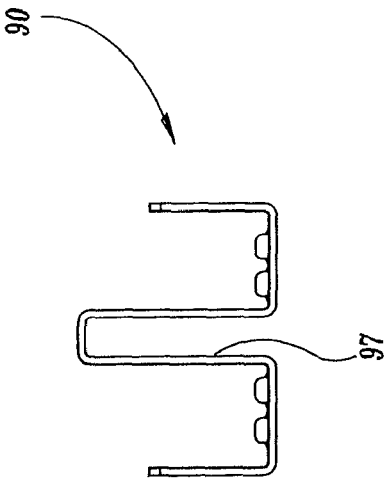
FIG. 9 is a front end view of the preformed anvil plate illustrated in FIGS. 7 and 8.
Figure 10:
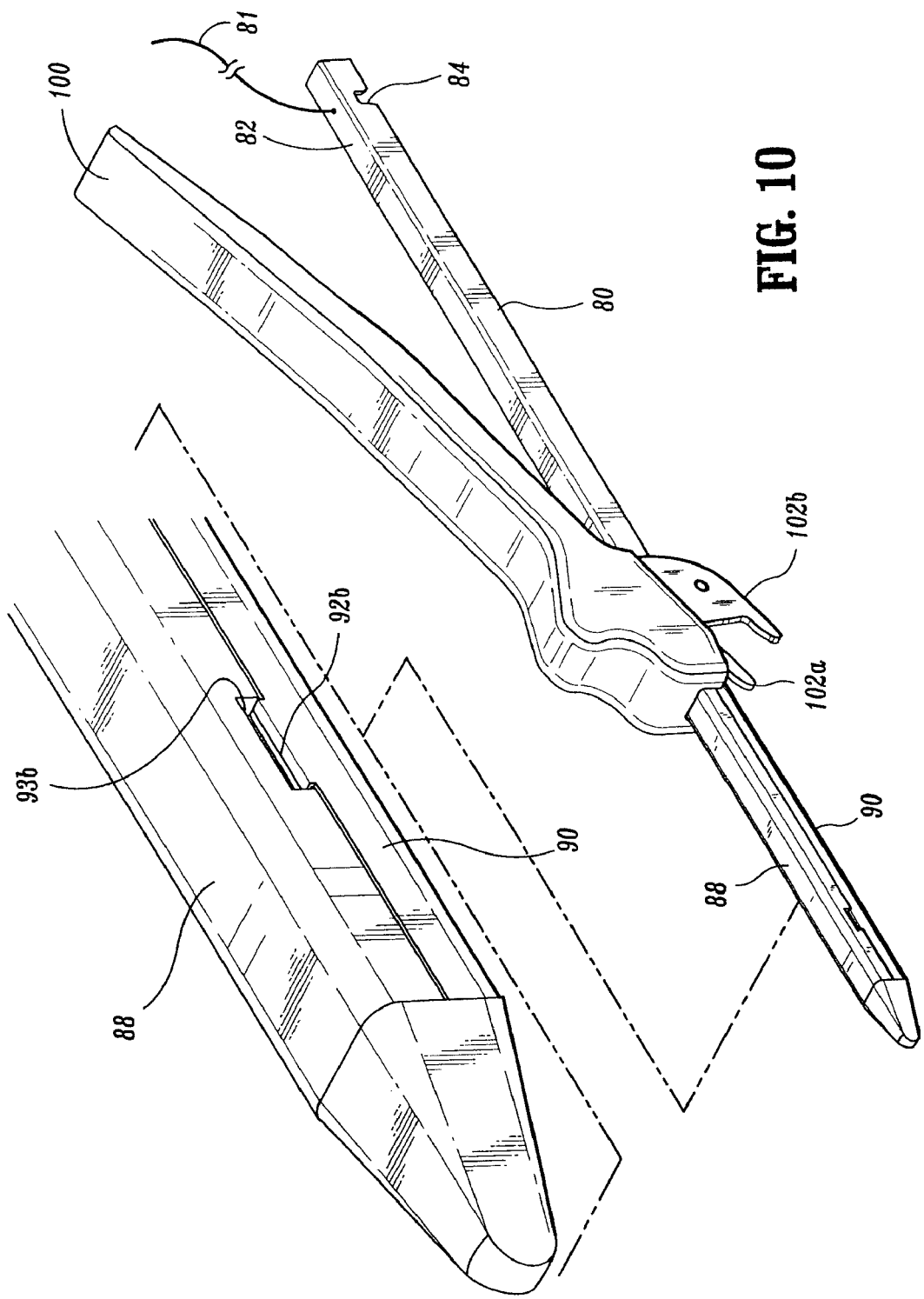
FIG. 10 is a perspective view of the upper body portion of the electrosurgical stapling apparatus of FIGS. 1A and 1B with an enlarged localized view of a distal portion thereof illustrating the connective engagement between the anvil plate and the anvil support beam.

Referring to FIGS. 7 and 8, anvil plate 90 is formed from a unitary piece of metal (conductive material) and is cold formed and stamped to define a plurality of staple forming recesses, pockets or cups 91. Each staple forming recess corresponds to a particular staple housed within cartridge 22. Anvil plate 90, as shown in FIG. 2, is provided with two opposed tangs 92a and 92b which extend inwardly to engage complementary engagement slots 93b (only one is shown) in anvil support beam 80 during fabrication and assembly (see FIG. 10). The cross-sectional configuration of anvil plate 90 is dimensioned to complement the cross-sectional geometry of support beam 80 (see FIG. 9). More particularly, cavity 97 which extends along the length of anvil plate 90 corresponds to a similar channel formed in support beam 80. These areas accommodate shank 35 and knife blade 36 as it translates distally to form an incision in stapled body tissue during a stapling operation.

Surfaces 97a of cavity 97, in one embodiment, can be energized for energizing knife blade 36 as it translates distally abutting surfaces 97a of cavity 97. In another embodiment as shown by FIG. 9B, surfaces 97a of cavity 97 are insulated by insulation material 89, such as Teflon, plastics (PVC), etc., to prevent an energized anvil plate 90 from energizing knife blade 36 or tissue within cavity 97.

A pair of rectangular apertures 95a and 95b are formed in anvil plate 90 adjacent the proximal end thereof for receiving a pair of correspondingly positioned flanges or projections 96a and 96b which project upwardly away from the tissue contacting surface (see FIGS. 2 and 4C). The interaction between aperture 95a, 95b and flanges 96a, 96b ensures that cartridge 22 and anvil plate 90 are property aligned with one another during a stapling procedure. Flanges 96a, 96b are spaced proximally of tissue stop portion 61 of retention channel 14. Portion 61 and the distal edge 13 of handle portion, best seen in FIG. 3, cooperate to prevent tissue from extending proximally.

At least one return wire 81 is connected to anvil support beam 80 and to the external generator for bipolar operation when the generator is activated. Bipolar operation is achieved via wire 47, actuation channel 44 and its associated structures, anvil plate 90 and its associated structures, anvil support beam 80, and wire 81. The non-conductive mounting block 49 as well as other non-conductive member or surfaces, such as the top surface of protective housing 25, insulates the conductive members of anvil half-section 11b with the conductive members of cartridge half-section 11a. It is contemplated that return wire 81 can be removed for monopolar operation. It is further contemplated that other types of thermogenic energy can be applied besides radiofrequency energy, such as pure thermal and resistive heating.

Figure 9D:
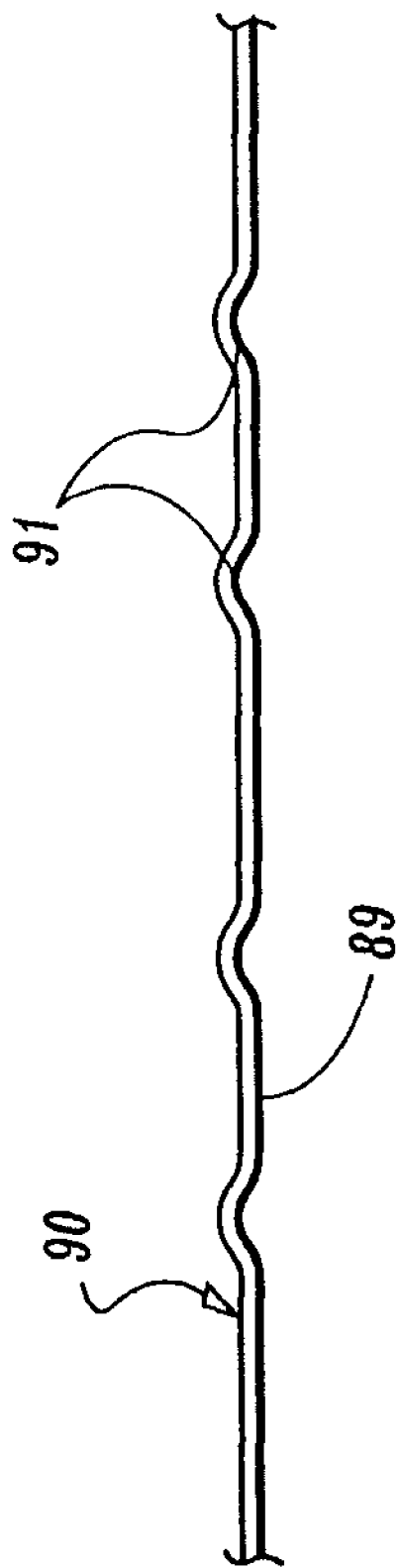
FIG. 9D is a cross-sectional view of a portion of the preformed anvil plate illustrated in FIGS. 7A and 8A having an insulation material applied thereon and within staple-forming cups.

It is further contemplated to connect the at least one return wire 81 to a component other than anvil support beam 80, such as anvil half-section 11b, for energizing staples 24 via an anvil half-section structure, such as anvil plate 90. In this embodiment, anvil plate 90 is energized which in turn energizes surgical staples 24 as they contact anvil plate 90 during surgical stapling. It is preferred to coat metallic anvil plate 90 with an insulating material 89 (see FIGS. 7A-9B and FIG. 9D), such as Teflon, soft plastics (PVC), etc., to prevent the energized anvil plate 90 from energizing tissue which is contacted by anvil plate 90. FIG. 9D is an enlarged view of a portion of FIG. 8A showing insulating material 89 coating staple-forming cups 91 of anvil plate 90. In FIGS. 7A-9C, the same reference numerals as in FIGS. 7-9 designate the same or similar components.

During a surgical stapling procedure, as staples 24 are ejected against anvil plate 90, staples 24 scratch off insulation coating or material 89 and make contact with metallic anvil plate 90, thus becoming energized. In the alternative, staple-forming cups 91 of anvil plate 90 are not coated (see FIG. 9C), such that staples 24 do not need to scratch off the insulation coating or material 89. The rest of anvil plate 90, however, is insulated by coating it with insulating material 89.

Referring again to FIG. 2, anvil half-section 11b of stapling apparatus 10 further includes clamping handle 100 which is used to securely clamp tissue between the staple forming surface of anvil plate 90 and the tissue contacting surface of cartridge 22. Clamping handle 100 is pivotably mounted to anvil support beam 80 about a transverse pivot pin which is not shown in the drawings. A pair of clamping hooks 102a and 102b depend from clamping handle 100 for interacting with U-shaped clamping beam 104 supported within the internal cavity defined in handle portion 12.

When apparatus 10 is assembled prior to use, notched area 84 at proximal end 82 of anvil support beam 80 is engaged with the cooperating detents 86 in the inner cavity 15 of body portion 12. Thereupon, anvil half-section 11b is mated with cartridge half-section 11a, and clamping handle 100 is disposed in the upright unclamped position shown in FIG. 1A. Subsequently, when body tissue is properly disposed between the staple forming surface of anvil plate 90 and the tissue contacting surface of cartridge 22, anvil half-section 11b is pivoted towards cartridge half-section 11a, about the detents in body portion 12, such that the distal ends of clamping hooks 102a and 102b are positioned immediately adjacent the proximal end of the base of U-shaped clamping beam 104. Concomitantly, flanges 96a and 96b engage apertures 95a and 95b in anvil plate 90 to ensure proper alignment of the anvil and the cartridge.

Then, to securely clamp the captured body tissue, clamping handle 100 is pivoted from the position illustrated in FIG. 1A to that which is shown in FIG. 1B. At such a time, clamping hooks 102a and 102b engage the base of clamping beam 104, locking the apparatus in a clamped condition. During clamping, the captured body tissue exerts a counter-force against the tissue contacting surface of cartridge 22 and the fastener forming surface of the anvil plate 90, urging the two structures apart. To overcome these forces and prevent the proximal portion 82 of anvil support beam 80 from bending, bearing surfaces are defined within retention channel 14 to support the compressive forces generated during clamping. In particular, as illustrated in FIG. 4A, opposed bearing shelves 110a and 110b are stamp formed in opposed walls 62 and 64 of retention channel 14. The bearing shelves are positioned to abut the medial section of anvil support beam 80 proximate the clamping handle pivot point.

Figure 11:
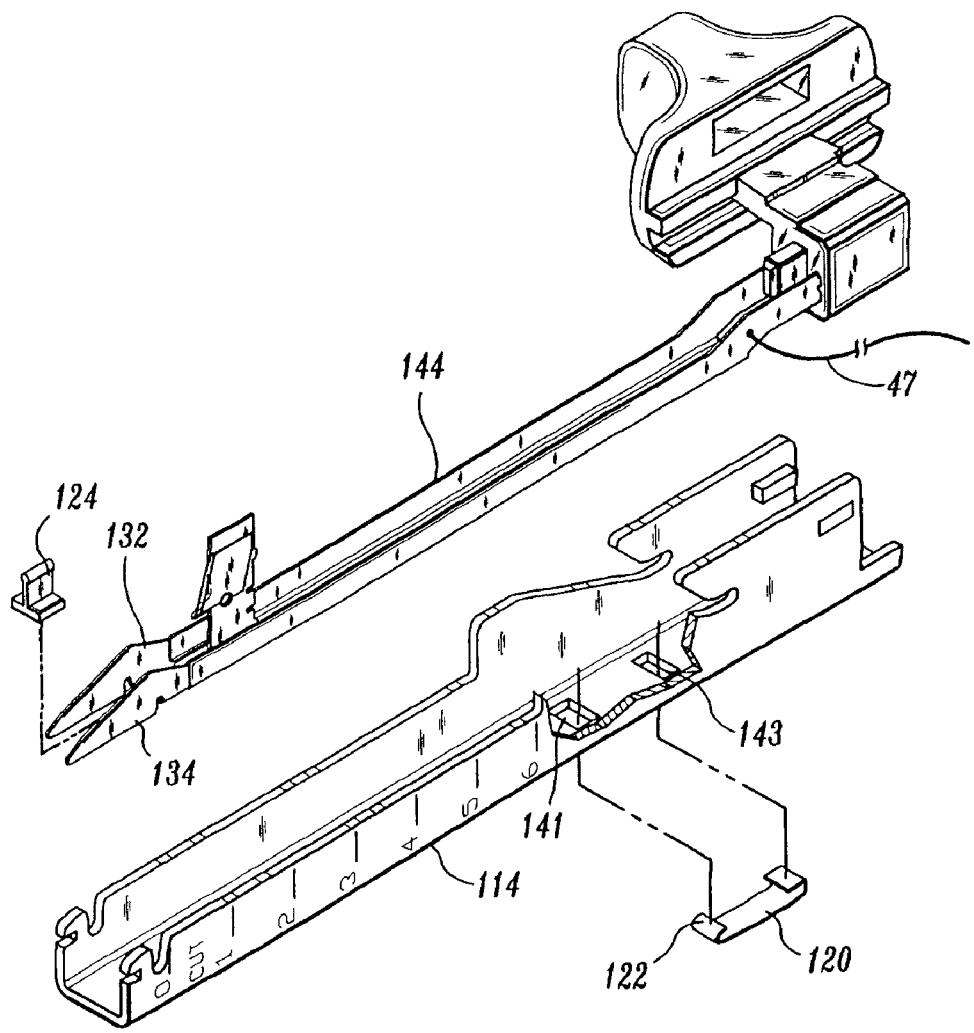
FIG. 11 is an exploded perspective view of an embodiment utilizing a lockout mechanism to prevent reactuation of the apparatus.
Figure 11A:
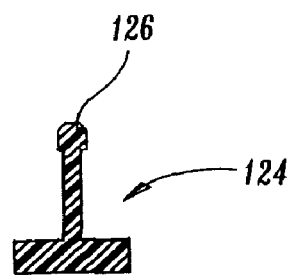
FIG. 11A is an enlarged cross-sectional view of the T-shaped member of the lockout mechanism.

It may also be desirable to provide a locking mechanism to prevent reactuation of the apparatus after it has been actuated. For example, a locking member 120 shown in FIG. 11 can be positioned in the retaining channel 114. Locking member 120 is biased to an upward engagement position and each end extends through a window 141, 143 in the channel 114. A T-shaped member 124 is positioned between the cam wedges 132, 134 to bias the hook portion 122 out of engagement with the actuation channel 144. Head portion 126 of T-shaped member 124 (FIG. 11A) is initially retained in the cartridge by a pair of detents in the cartridge which extend into the knife slot. When the apparatus is actuated, head portion 126 of T-shaped member 124 is in the knife slot.

Figure 12:
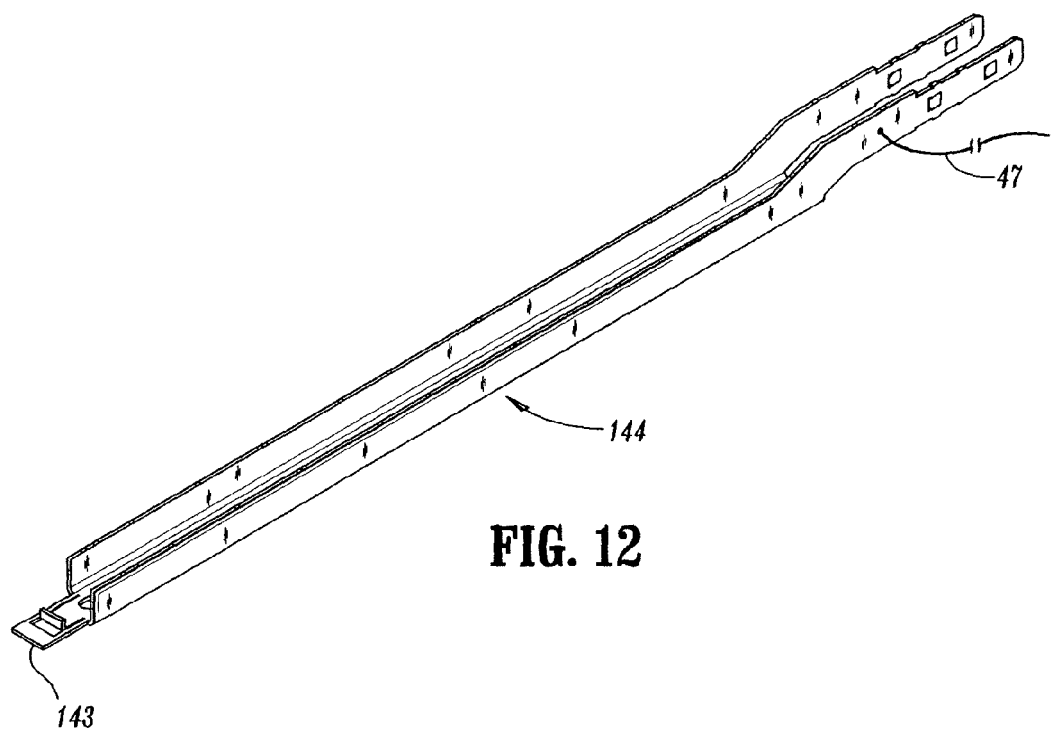
FIG. 12 is an enlarged perspective view of the actuation channel having an edge for engagement by the hook of the lockout mechanism.
Figure 13A:
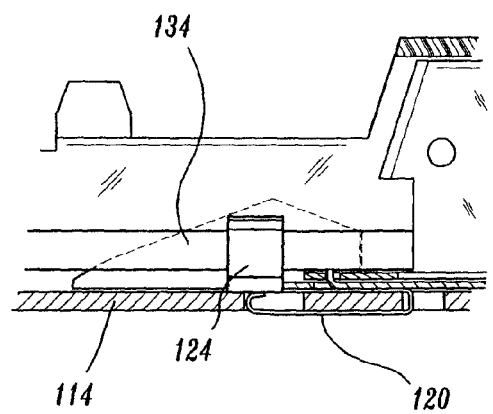
FIGS. 13A and 13B are side views of the lockout mechanism illustrating its movement from a non-engaged to an engaged position.
Figure 13B:
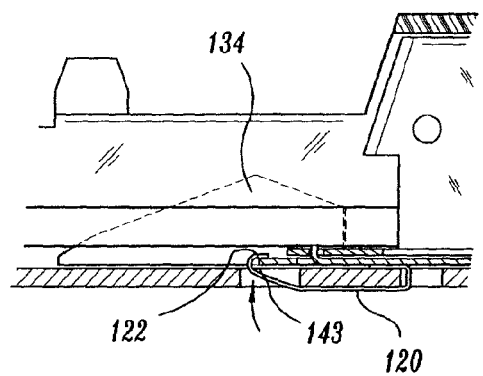

A second pair of detents (not shown) at the distal end of the knife slot engages head portion 126 of T-shaped member 124 to hold it at the distal end of cartridge 122 when cam wedges 132, 134 are advanced to the distal position. When actuation channel 144 is retracted from the post-actuated position to the pre-actuated position, T-shaped member 124 remains forward allowing hook portion 122 to return to the upward position and extend through the window 141 in retaining channel 114 to engage edge 143 (see FIGS. 12 and 13A) of actuation channel 144 to prevent advancement of the actuation channel. FIGS. 13A, 13B illustrate movement of the locking member 120 from an initial non-engaged position (FIG. 13A) out of engagement with actuation channel 144 to an engaged position (FIG. 13B) in engagement with actuation channel 144 to prevent distal movement thereof.

Figure 14:
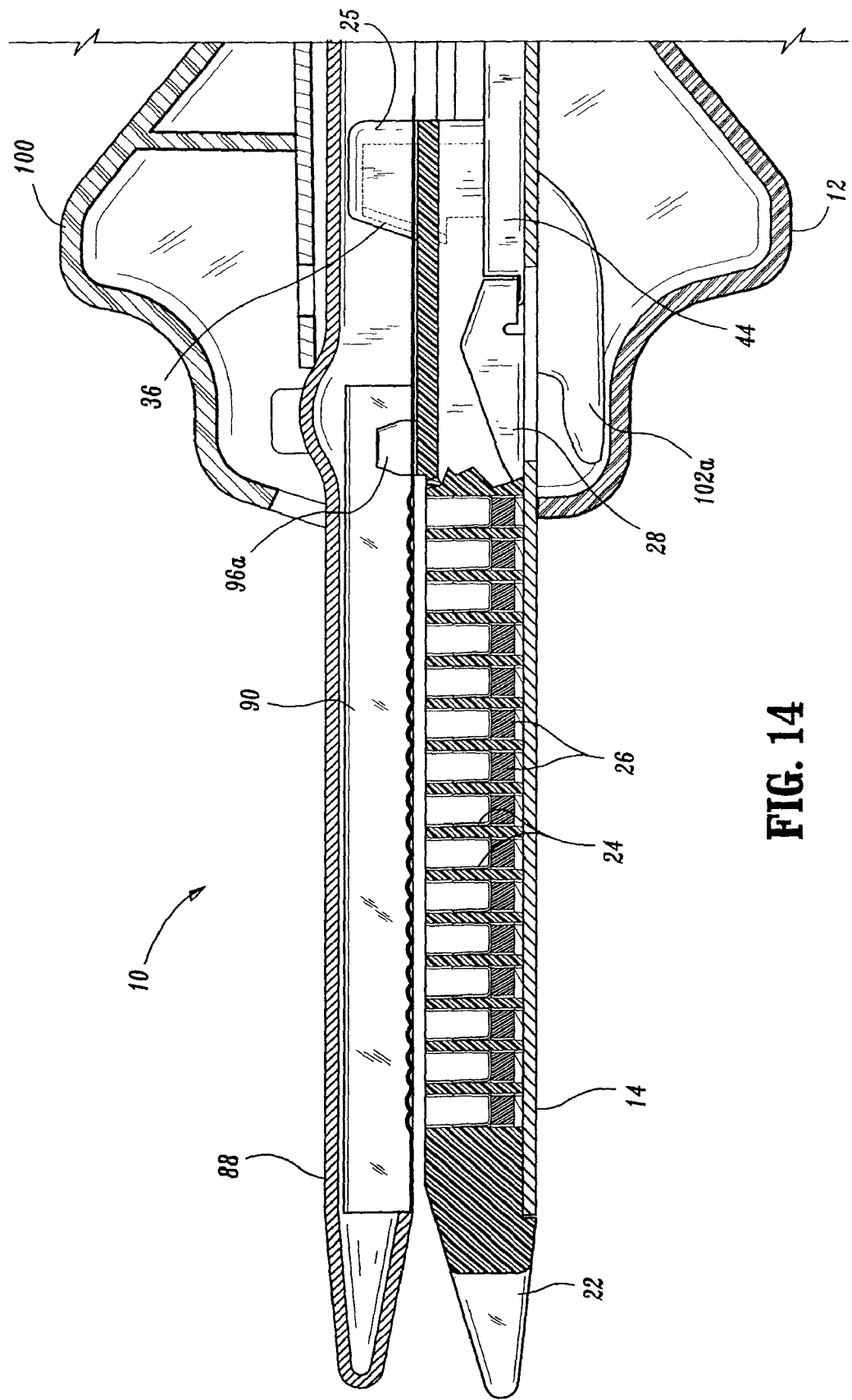
FIG. 14 is a side elevational view in cross-section of the electrosurgical stapling apparatus of the present invention with the actuation sled disposed in a pre-actuated proximal position.
Figure 15:
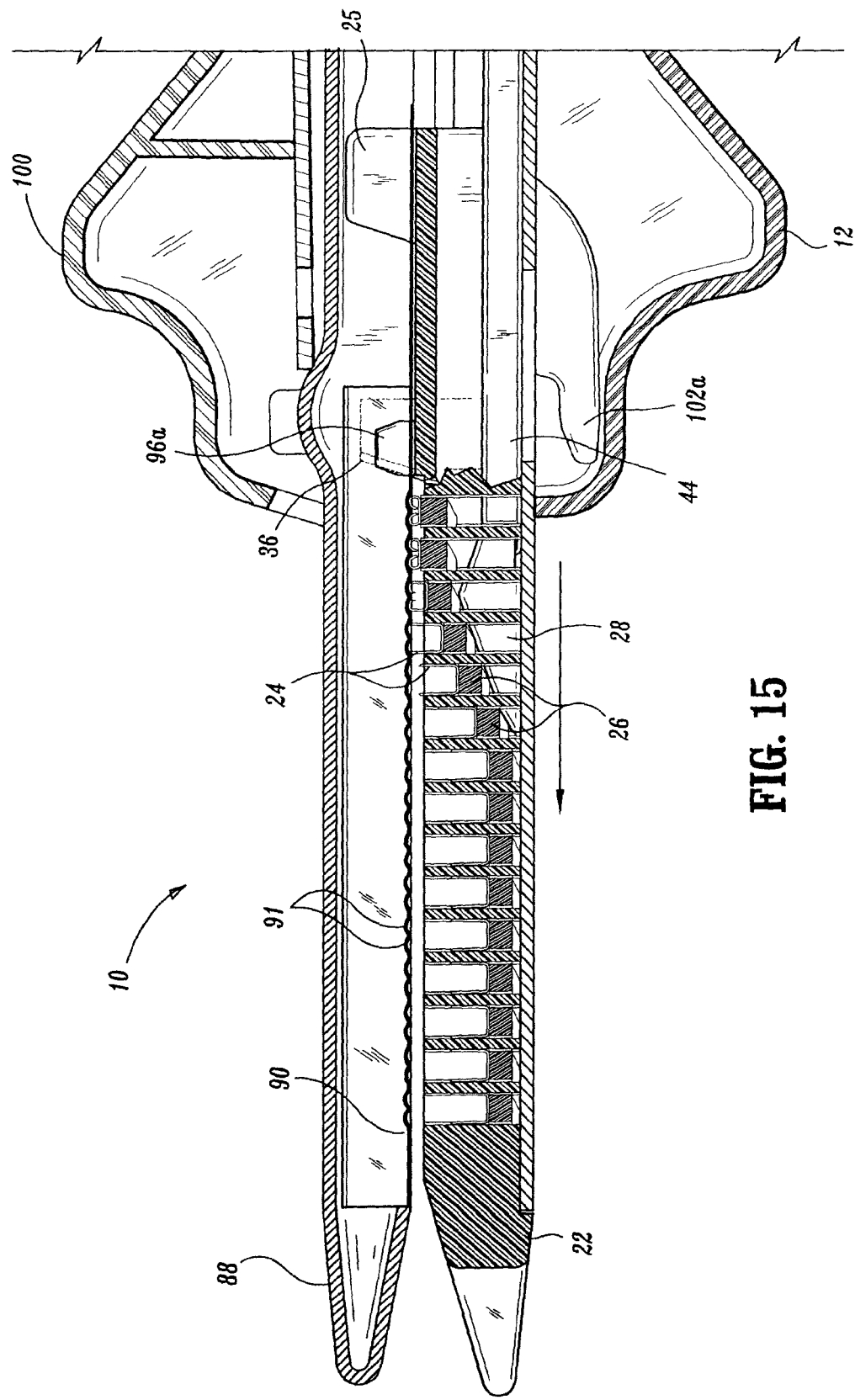
FIG. 15 is a side elevational view in cross-section of the electrosurgical stapling apparatus of the present invention with the actuation sled disposed in a partially advanced position.
Figure 16:
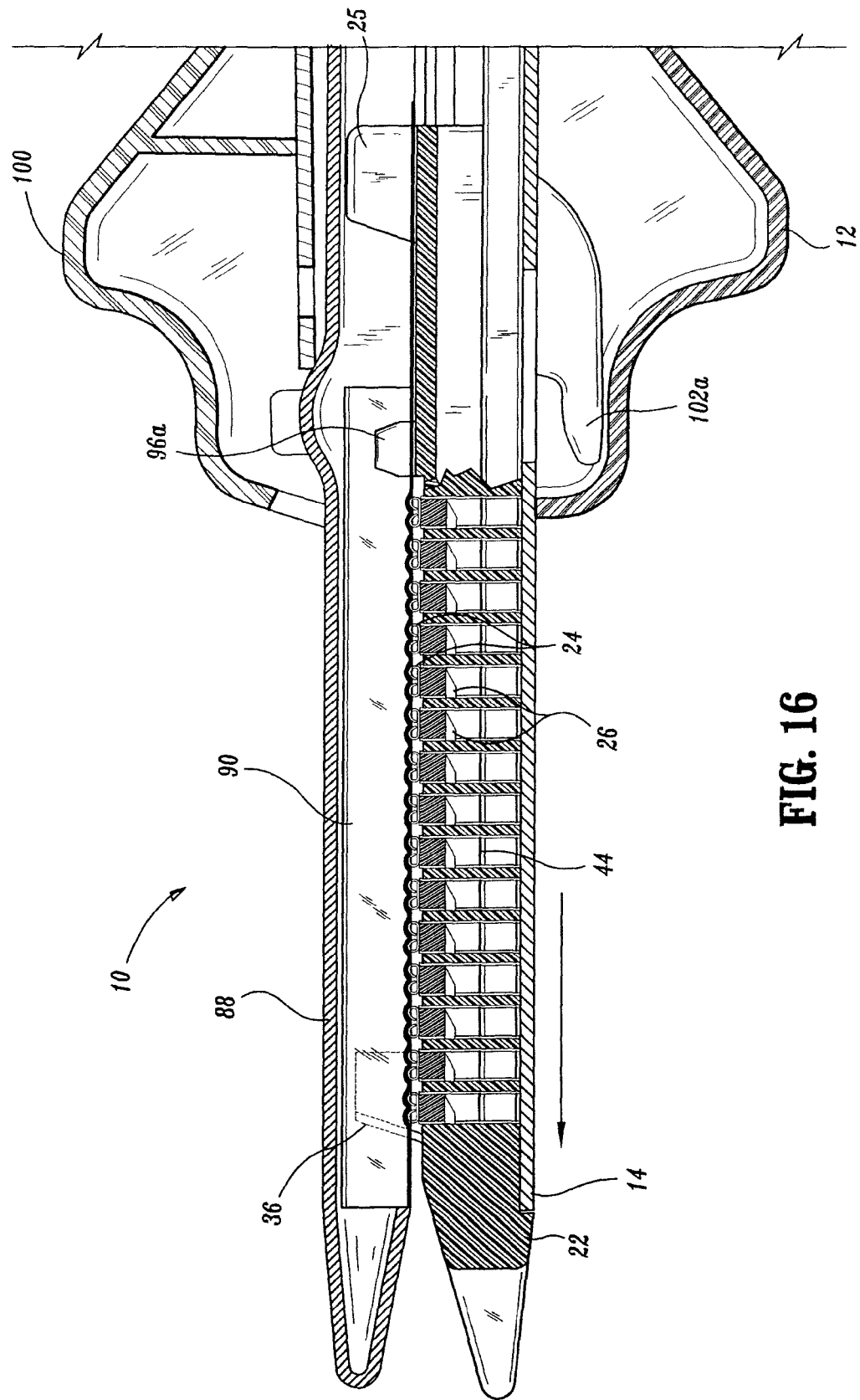
FIG. 16 is a side elevational view in cross-section of the electrosurgical stapling apparatus of the subject application with the actuation sled advanced to the distal end of the cartridge at the conclusion of a staple firing procedure.

Referring now to FIGS. 14-16, there is illustrated, in sequential order, a staple firing operation in which a plurality of staples are ejected from cartridge 22 and driven against the staple forming surface of anvil plate 90. In operation, prior to firing electrosurgical stapling apparatus 10, actuation sled 28 is in the proximal-most position shown in FIG. 14. At such a time, knife blade 36 is enclosed in protective housing 25 formed adjacent the proximal end of disposable loading unit 20. To fire the apparatus, firing knob 50 is moved in a distal direction. Accordingly, as illustrated in FIG. 15, actuation channel 44 drives actuation sled 28 distally into and through cartridge 22. During its distal translation, the angled leading surfaces of cam wedges 32 and 34 sequentially contact ejectors 26, urging them in a direction transverse to the direction of movement of actuation sled 28. As a result, ejectors 26 push staples 24 from their individual slots, driving each staple into a respective staple forming cup 91 in anvil plate 90.

Sequential firing of the staples continues until actuation sled 28 is advanced to the distal end of cartridge 22, at which time, all of the staples once housed within cartridge 22 will have been ejected (see FIG. 16). Thereafter, firing knob 50 is retracted to its original position, the cartridge and anvil sections are separated, and the spent disposable loading unit 20 is removed from retaining channel 14. Subsequently, a new, fully loaded disposable loading unit 20 can be positioned in retaining channel 14 such that the slot 40 of actuation sled 28 engages flange or engagement member 42 of actuation channel 44 to enable re-use of the apparatus.

It is provided that the thermogenic energy applied to actuation channel 44 also energizes the top surface of cartridge 22 and thermogenic energy applied to anvil support beam 80 or anvil half-section 11b energizes anvil plate 90. Accordingly, the top surface of cartridge 22 and anvil plate 90 behave in effect as two opposing electrodes for sealing tissue therebetween prior to being stapled and/or cut. Also, if disposable loading unit 20 has been spent, the apparatus 10 can just be used for sealing tissue by using the top surface of cartridge 22 and anvil plate 90 as the electrodes.

The thermogenic energy can be monopolar or bipolar radiofrequency, pure thermal, and resistive heating, and is applied to the stapling apparatus to energize or heat the staples either directly and/or via one or more conductive members before, during, and/or after the apparatus has stapled, cauterized, and/or cut tissue. It is further provided to equip the apparatus of the present invention with an impedance or other feedback mechanism for monitoring at least one characteristic, such as voltage and current transients across the tissue, for improved tissue sealing.

Another preferred embodiment of the disclosure will now be described with reference to FIGS. 17-19. FIGS. 17 and 18 illustrate a fastener applying device shown generally as 200. Fastener applying device 200 includes a housing 212 including stationary handle 214, a distally extending body portion 216, and a transverse body portion 215. Transverse body portion 215 is configured to receive support frame 218. Housing 212 may be constructed from plastic material in the form of molded housing half-sections 212a and 212b. Housing half-sections 212a and 212b are fastened together by a plurality of screws 219. Preferably, housing 212 is constructed from fiberglass reinforced plastic, although other materials having the requisite strength requirements may be used.

Figure 19:
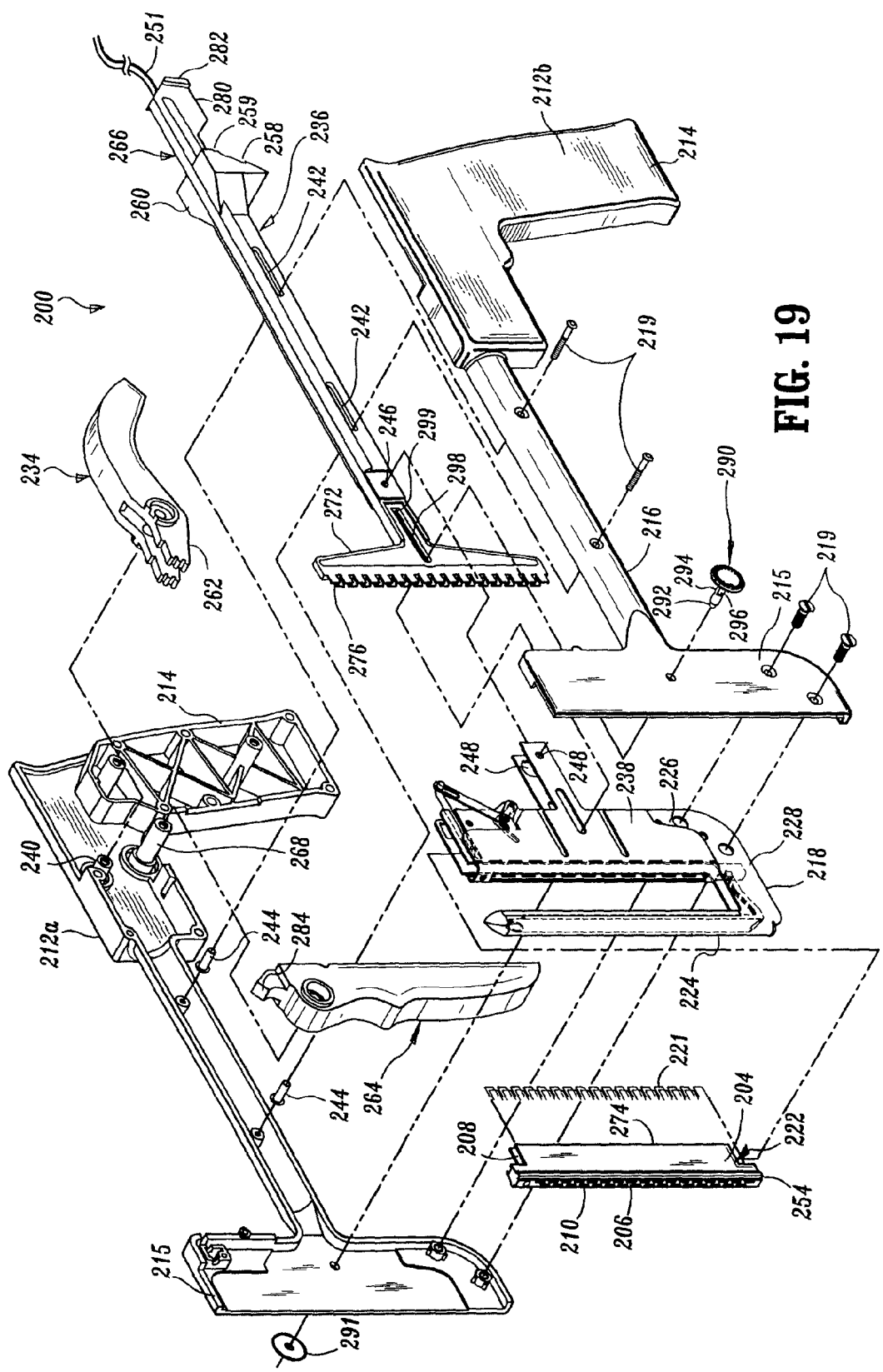
FIG. 19 is an exploded perspective view of the device shown in FIG. 17.

FIG. 19 illustrates a perspective view of fastener applying device 200 with the internal components of device 200 separated from each other. The device 200 may be is fastened together using screws 219 that extend between housing half-sections 212a and 212b, although adhesives, ultrasonic welding, and other known fastening methods may also be used to fasten the components of the device together.

An anvil (not shown) is fastened to a first leg 224 of the support frame 218. Any known fastening technique may be used to fasten the anvil to first leg 224. The support frame 218 is substantially U-shaped and includes first leg 224, a second leg 226, and a base portion 228. First leg 224 extends substantially parallel to second leg 226. The support frame 218 may be monolithically formed by bending a sheet of material into the desired shape. Preferably, support frame 218 is constructed from stainless steel, although other materials having the requisite strength requirements may be used.

Cartridge carrier 238 is slidably supported about second leg 226 of support frame 218 and is movable towards first leg 224. Cartridge assembly 222 includes a body 204 having a distal face 206 which is spaced from an open proximal end 274. A pusher bar channel 208 extends from the open end 274 through a portion of body 204. A plurality of slots 210 house fasteners 221 (FIG. 19) and are configured to receive distally extending fingers 276 of pusher bar 266. The slots 210 extend between the distal end of pusher bar channel 208 and the distal face 206 of cartridge assembly 222. The outer surface of cartridge body 204 includes a pair of transversely extending flanges 254. Cartridge carrier 238 is provided with means for receiving and supporting cartridge assembly 222.

The fastener applying device 200 has an approximation mechanism for advancing cartridge assembly 222 and cartridge carrier 238. An approximating clamp 234 or lever is pivotably mounted about pivot member 240 which is supported between housing half sections 212a and 212b in the proximal end of housing 212. The approximating clamp 234 is movable into engagement with a proximal end of clamp slide 236 to linearly advance the clamp slide 236 within body portion 216. A plurality of longitudinal slots 242 formed in clamp slide 236 are configured to receive guide pins 244 to limit clamp slide 236 to a linear path of travel.

The distal end of clamp slide 236 includes a pair of projections 246. The projections 246 are fastened within a pair of openings 248 formed in a proximal end of cartridge carrier 238, such that linear movement of clamp slide 236 is translated to corresponding linear movement of cartridge carrier 238.

Referring to FIG. 19, approximating clamp 234 includes an abutment end 262 having a series of detents which are configured to be received in recesses 258 and 259 formed in an angled proximal end 260 of clamp slide 236. The angled proximal end 260 of the clamp slide 236 and the abutment end 262 of the approximating clamp 234 are movable into engagement to advance the cartridge assembly 222 towards the anvil. Preferably, approximating clamp 234 is constructed of plastic and clamp slide 236, cartridge carrier 238 and pusher bar 266 are constructed of stainless steel. A proximal end of pusher bar 266 is connected to a wire 251 for energizing pusher bar 266 and clamp slide 236 and in turn energizing the distal end of pusher bar 266 which includes energizing distally extending fingers 276. Wire 251 is preferably connected to an electrosurgical generator for providing electrical energy to pusher bar 266.

It is contemplated that wire 251 can be connected to any part of device 200, such as first leg 224 and the metallic anvil, for energizing the fasteners via these members. For example, the anvil is energized which in turn energizes the fasteners as they contact a surface of the anvil during surgical stapling. It is preferred to coat the metallic anvil plate with an insulating material, such as Teflon, soft plastics (PVC), etc., to prevent the energized anvil from energizing tissue which is contacted by the anvil.

During a surgical stapling procedure, as the fasteners are ejected against a surface of the anvil, the fasteners scratch off the insulation coating and make contact with the anvil, thus becoming energized. In the alternative, staple-forming cups or pockets of the anvil are not coated, such that the fasteners do not need to scratch off the insulation coating. The rest of the anvil, however, is insulated.

FIG. 19 illustrates the firing mechanism for applying the fasteners of device 200. The firing mechanism includes a trigger actuator 264 and elongate pusher bar 266 slidably received in a channel formed in clamp slide 236. Trigger actuator 264 is pivotable about pivot pin 268 into engagement with a proximal end of pusher bar 266 to advance pusher bar 266 with respect to cartridge carrier 238. Pivot pin 268 is supported between housing half-sections 212a and 212b.

The slots 242 of pusher bar 266 slidably receive the guide pins 244. Guide pins 244 limit pusher bar 266 to a linear path of travel identical to that of clamp slide 236. The distal end of pusher bar 266 is formed with a head portion 272 configured to move through the open proximal end 274 of cartridge assembly 222 to effect ejection of fasteners 221. The plurality of distally extending fingers 276 are integrally formed on head portion 272. Each finger 276 has a concave distal surface configured to engage the fasteners 221 housed within cartridge assembly 222 and energize the fasteners 221. Fingers 276 extend from head portion 272 in a pattern that corresponds to the pattern that fasteners 221 are housed within cartridge assembly 222. For example, the pattern may be two staggered rows. Other patterns are also contemplated.

As illustrated in FIG. 19, the proximal end of pusher bar 266 has a locking surface 280 and a contact surface 282. The trigger actuator 264 includes an engagement surface 284 which pivots into engagement with contact surface 282 of the pusher bar 266 to advance the pusher bar 266 distally.

When the pusher bar 266 is in a retracted position, locking surface 280 of the pusher bar 266 is positioned to prevent engagement between engagement surface 284 of the trigger actuator 264 and contact surface 282 of pusher bar 266. Thus, locking surface 280 prevents firing fasteners 221 prior to sufficient approximation of cartridge assembly 222 and the anvil. Before trigger actuator 264 can be rotated counter-clockwise to eject fasteners 221 from device 200, the approximating clamp 234 must be rotated clockwise toward the stationary handle 214 to advance clamp slide 236 distally. This frees trigger actuator 264 for pivotal movement to fire the fasteners 221.

An adjustment member 290 is provided in the distal end of the device 200 to facilitate ejection of fasteners 221 from fastener applying device 200. Adjustment member 290 includes a cylindrical shaft 292 having a pair of diametrically opposed first and second flats 294 and 296, respectively. Cylindrical shaft 292 extends through an opening formed in the second leg 226 of support member 218 and through the distal end of a longitudinal adjustment slot 298 formed in pusher bar 266. The adjustment member 290 is secured to support member 218 by adjustment nut 291. Shaft 292 is rotatable to align one of the opposed flats 294 or 296 with a proximal end 299 of adjustment slot 298 to define a stop surface for the pusher bar 266. Since the flats 294 and 296 are formed at different depths into the cylindrical shaft 292, shaft 292 may be rotated to change the position of the stop surface to vary the stroke of the pusher bar 266.

An alignment mechanism is operatively connected to the approximation mechanism to maintain alignment between cartridge assembly 222 and the anvil during approximation of the anvil and cartridge 222. A more detailed description of a similar fastener applying device as device 200 is found in U.S. Pat. No. 5,964,394 having a common assignee as the present application. The entire contents of U.S. Pat. No. 5,964,394 are incorporated herein by reference.

Figure 20:
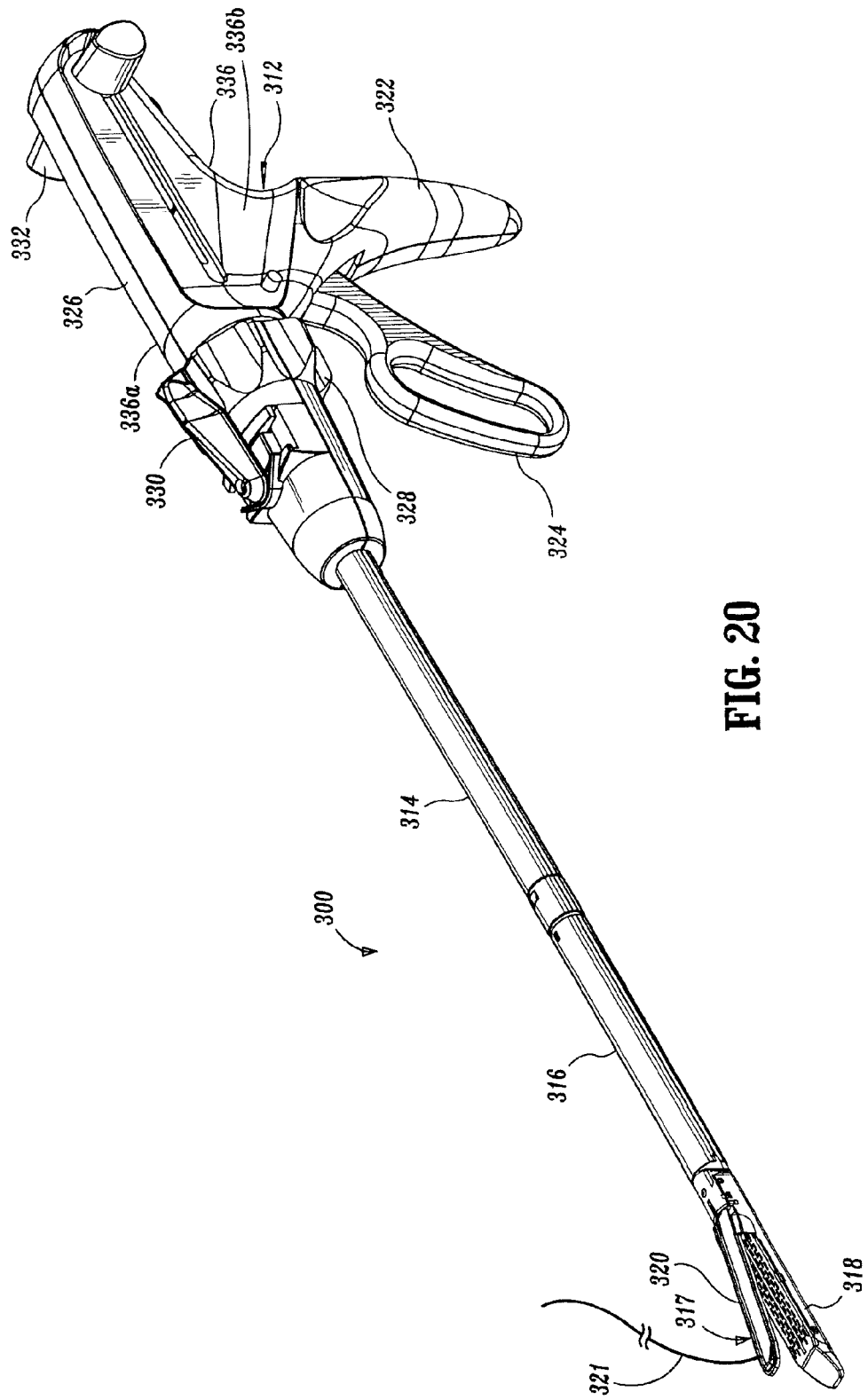
FIG. 20 is a perspective view of an electrosurgical stapling apparatus constructed in accordance with another preferred embodiment.
Figure 21:
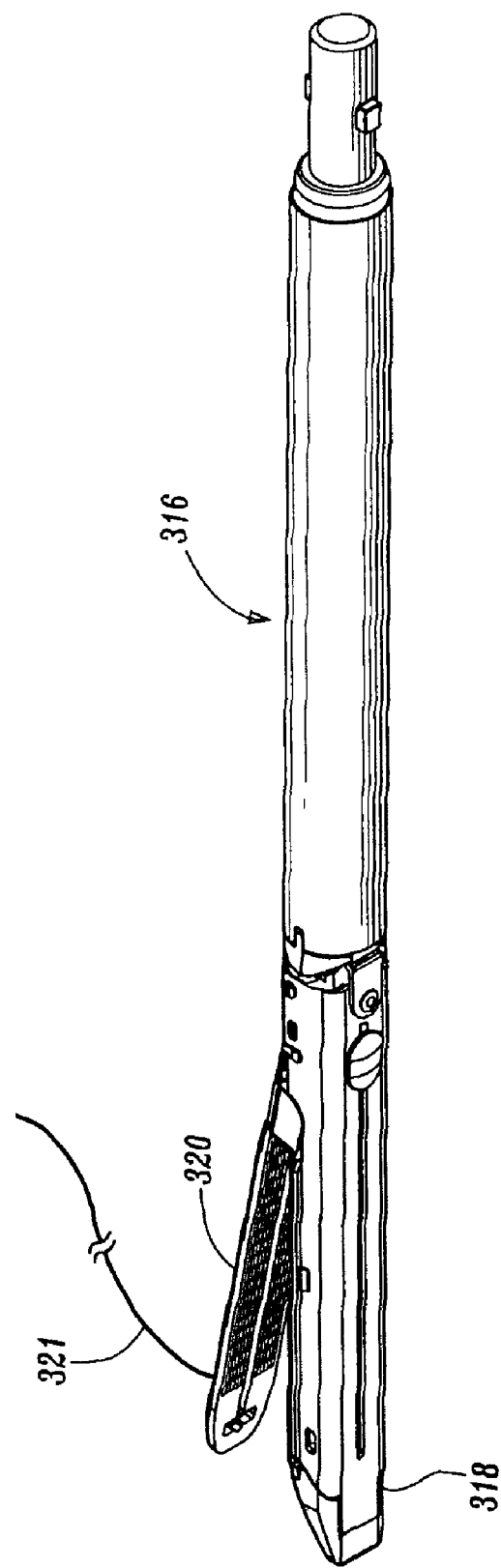
FIG. 21 is an enlarged perspective view of an end effector of the device shown in FIG. 20.

With reference to FIGS. 20 and 21 there is shown another preferred embodiment of the disclosure having a monopolar arrangement as device 200. FIGS. 20 and 21 illustrate a fastener applying device shown generally as 300. Surgical stapling apparatus 300 includes a handle assembly 312 and an elongated body 314. A disposable loading unit or DLU 316 is releasably secured to a distal end of elongated body 314. DLU 316 includes a tool assembly 317 having a cartridge assembly 318 housing a plurality of metallic surgical staples and an anvil assembly 320 movably secured in relation to cartridge assembly 318. Anvil assembly 320 is metallic and is energized by a wire 321 connected thereto for energizing the staples during a stapling operation. DLU 316 is configured to apply linear rows of staples. Wire 321 is preferably connected to an electrosurgical generator for providing electrical energy to anvil assembly 320. It is contemplated that wire 321 can be connected to any part of apparatus 300 besides anvil assembly 320.

It is preferred to coat metallic anvil assembly 320 with an insulating material, such as Teflon, soft plastics (PVC), etc., to prevent the energized anvil assembly 320 from energizing tissue which is contacted by anvil assembly 320.

During a surgical stapling procedure, as the staples are ejected against a staple-forming surface of anvil assembly 320, the staples scratch off the insulation coating and make contact with anvil assembly 320, thus becoming energized. In the alternative, staple-forming cups or pockets of anvil assembly 320 are not coated, such that the staples do not need to scratch off the insulation coating. The rest of anvil assembly 320, however, is insulated.

Handle assembly 312 includes a stationary handle member 322, a movable handle member 324, and a barrel portion 326. Handle assembly 312 includes housing 336, which is preferably formed from molded housing half-sections 336a and 336b, which forms stationary handle member 322 and barrel portion 326 of handle assembly 312. Movable handle member 324 is pivotably supported between housing half-sections 336a and 336b.

A rotatable member 328 is preferably mounted on the forward end of barrel portion 326 to facilitate rotation of elongated body 314 with respect to handle assembly 312. An articulation lever 330 is also preferably mounted on the forward end of barrel portion 326 adjacent rotatable knob 328 to facilitate articulation of tool assembly 317. A pair of retraction knobs 332 are movably positioned along barrel portion 326 to return surgical stapling apparatus 300 to a retracted position as described in U.S. Pat. No. 6,330,965 B1 having a common assignee as the present application. The entire contents of U.S. Pat. No. 6,330,965 B1 are incorporated herein by reference.

Other types of staplers from those described herein can be designed to include energizing means for energizing the staples during a stapling procedure, such as circular and endoscopic staplers.

Although the subject apparatus has been described with respect to preferred embodiments, it will be readily apparent to those having ordinary skill in the art to which it appertains that changes and modifications may be made thereto without departing from the spirit or scope of the claims appended hereto.

The invention claimed is:

1. A surgical stapler, comprising:

an anvil member having a plurality of staple-forming recesses defined therein for deforming a corresponding plurality of surgical staples thereagainst, the anvil includes an electrically insulative material disposed on a tissue contacting surface thereof, wherein at least one of the plurality of staple-forming recesses is coated with the electrically insulative material, wherein the electrically insulative material is selectively removable, and wherein the electrically insulative material is selectively removed from the tissue contacting surface of the anvil member during a firing of the surgical stapler;

a cartridge assembly including a staple cartridge defining a tissue contact surface and configured to retain a plurality of electrically conductive surgical staples;

an electrical conduit adapted for connection to a surgical generator; and an actuator operatively connected to the cartridge assembly for deploying the plurality of surgical staples from the staple cartridge against the anvil member, the actuator being movable within the cartridge assembly and coupled to the electrical conduit, the actuator including an electrically conductive actuation sled and an electrically conductive knife blade, wherein the electrical conduit is configured for transmitting a thermogenic energy to the knife blade and to the staples through the actuation sled.

2. The surgical stapler according to claim 1, wherein at least one of the plurality of staple-forming recesses includes no electrically insulative material disposed thereon.

3. The surgical stapler according to claim 1, wherein at least one of the plurality of staple-forming recesses is formed of an electrically conductive material.

4. The surgical stapler according to claim 1, wherein the thermogenic energy transmitted is selected from the group consisting of radiofrequency, thermal, and resistive heating.

5. The surgical stapler according to claim 1, wherein the staple cartridge includes a longitudinal slot wherein the knife blade traverses through said longitudinal slot, and wherein the knife blade delivers at least a portion of the thermogenic energy to tissue along at least one cut line during a firing of the surgical stapler.

6. The surgical stapler according to claim 1, wherein the actuation sled defines a shank, and wherein the actuation sled traverses through a longitudinal slot of the anvil plate and the staple cartridge.

* * * * *